United States Patent
Sumida

(10) Patent No.: US 10,449,345 B2
(45) Date of Patent: Oct. 22, 2019

(54) MICRONEEDLE PUNCTURE INSTRUMENT

(71) Applicant: TOPPAN PRINTING CO., LTD., Tokyo (JP)

(72) Inventor: Tomoya Sumida, Tokyo (JP)

(73) Assignee: TOPPAN PRINTING CO., LTD., Tokyo (JP)

(*) Notice: Subject to any disclaimer, the term of this patent is extended or adjusted under 35 U.S.C. 154(b) by 0 days.

(21) Appl. No.: 16/240,740

(22) Filed: Jan. 5, 2019

(65) Prior Publication Data

US 2019/0134370 A1 May 9, 2019

Related U.S. Application Data

(63) Continuation of application No. PCT/JP2017/025732, filed on Jul. 14, 2017.

(30) Foreign Application Priority Data

Jul. 15, 2016 (JP) .................................. 2016-140500

(51) Int. Cl.
*A61M 37/00* (2006.01)
*A61M 5/42* (2006.01)

(52) U.S. Cl.
CPC .......... *A61M 37/0015* (2013.01); *A61M 5/42* (2013.01); *A61M 37/00* (2013.01);
(Continued)

(58) Field of Classification Search
CPC . A01K 11/005; A61B 5/150984; A61B 5/685; A61B 17/205; A61M 5/42;
(Continued)

(56) References Cited

U.S. PATENT DOCUMENTS 4,392,493 A * 7/1983 Niemeijer ............ A61B 17/205
606/116
6,743,211 B1 * 6/2004 Prausnitz ........... A61B 5/14514
604/239

(Continued)

FOREIGN PATENT DOCUMENTS

JP 2009-516572 A 4/2009
WO WO-2015/115113 A1 8/2015

OTHER PUBLICATIONS

International Searching Authority, "International Search Report," issued in connection with International Patent Application No. PCT/JP2017/025732, dated Oct. 17, 2017.
(Continued)

*Primary Examiner* — Bhisma Mehta
*Assistant Examiner* — Larry R. Wilson
(74) *Attorney, Agent, or Firm* — Foley & Lardner LLP

(57) ABSTRACT

A microneedle puncture instrument includes a pinch section including a first pinch element and a second pinch element arrayed in an array direction and configured to individually pinch the skin in a pinch direction, which intersects with the array direction, the first pinch element and the second pinch element being connected to each other with a distance therebetween maintained within a predetermined range; and a puncture section configured to puncture the skin while pinching the skin in the pinch direction at a position between the first pinch element and the second pinch element in the array direction, the puncture section including a microneedle for puncturing the skin and a support portion that supports the microneedle.

6 Claims, 12 Drawing Sheets

(52) U.S. Cl.
CPC ............... *A61M 2037/0023* (2013.01); *A61M 2037/0061* (2013.01)

(58) Field of Classification Search
CPC .............. A61M 5/425; A61M 37/0015; A61M 2037/0023–0061
See application file for complete search history.

(56) References Cited

U.S. PATENT DOCUMENTS

| | | | |
|---|---|---|---|
| 8,617,126 B2* | 12/2013 | Gross .................... | A61M 5/425 604/117 |
| 2007/0118077 A1 | 5/2007 | Clarke et al. | |
| 2011/0166509 A1 | 7/2011 | Gross et al. | |
| 2013/0190794 A1 | 7/2013 | Kendall et al. | |
| 2016/0331910 A1 | 11/2016 | Imai et al. | |

OTHER PUBLICATIONS

International Searching Authority, "Written Opinion," issued in connection with International Patent Application No. PCT/JP2017/025732, dated Oct. 17, 2017.

Extended European Search Report issued in corresponding European Patent Application Ser. No. EP84060, dated Jul. 1, 2019.

* cited by examiner

MICRONEEDLE PUNCTURE INSTRUMENT

CROSS-REFERENCE TO RELATED PATENT APPLICATIONS

This application is a continuation application filed under 35 U.S.C. § 111(a) claiming the benefit under 35 U.S.C. §§ 120 and 365(c) of International Patent Application No. PCT/JP2017/025732, filed on Jul. 14, 2017, which is based upon and claims the benefit of priority to Japanese Patent Application No. 2016-140500, filed on Jul. 15, 2016; the disclosures of which are all hereby incorporated herein by reference in their entireties.

TECHNICAL FIELD

The present invention relates to a microneedle puncture instrument for puncturing a microneedle into the skin.

BACKGROUND ART

Microneedles are known to be used for administration of drugs such as vaccines into the body. The microneedle includes a needle-shaped projection, and the projection has a length that does not reach nerve cells in the dermis layer of the skin. Accordingly, in the administration method using a microneedle, a skin puncture pain can be reduced compared with an administration method using an injection needle. Further, in the administration method using a microneedle, a drug is delivered into the intradermal layer of the skin which is abundant in antigen presenting cells. Accordingly, there is a possibility that the dose of drug can be reduced compared with the subcutaneous drug administration using an injection needle.

In drug administration using a microneedle, a puncture depth of the projection is controlled to a predetermined depth. However, since the projection has the length smaller than that of an injection needle, the projection may not be punctured into a desired depth due to deformation of the skin when the projection is merely pressed against the skin. Accordingly, an injection instrument having a limiter for controlling the depth of puncture into the skin by the projection and a stabilizer that surrounds the projection and reduces deformation of the skin around the projection may be used for microneedle puncture (for example, see PTL 1).

CITATION LIST

[Patent Literature] PTL 1: JP 2009-516572 A

SUMMARY OF THE INVENTION

Technical Problem

In order to hold the projection punctured into the skin having elasticity, it is required to continuously press the injection instrument against the skin with a force of a degree that prevents the projection from bouncing back due to the elasticity of the skin. However, since the injection instrument is pressed against the skin by a user, the amount of force that presses the injection instrument against the skin may vary or a position at which the injection instrument is pressed may vary while the injection instrument is pressed against the skin by the user. This may cause difficulty in holding the projection in a punctured state.

An object of the present invention is to provide a microneedle puncture instrument for holding the microneedle punctured into the skin.

Solution to the Problem

In order to address the above problem, an aspect of the invention includes: a microneedle puncture instrument including a pinch section including a first pinch element and a second pinch element arrayed in an array direction and configured to individually pinch the skin in a pinch direction, which intersects with the array direction, the first pinch element and the second pinch element being connected to each other with a distance therebetween maintained within a predetermined range; and a puncture section configured to puncture the skin while pinching the skin in the pinch direction at a position between the first pinch element and the second pinch element in the array direction, the puncture section including a microneedle for puncturing the skin and a support portion that supports the microneedle.

With this configuration, when the microneedle is punctured into the skin, the first pinch element and the second pinch element pinch the sites on both sides of a portion of the skin, which is a site to be punctured by the microneedle, so that the respective sites are fixed. Moreover, since the puncture section having the microneedle also pinches a portion located between the sites pinched by the respective pinch elements when the microneedle is punctured into the skin, the portion to be punctured by the microneedle is also fixed.

Thus, with this configuration, when and while the microneedle is punctured into the skin, a site of the skin to be punctured by the microneedle and sites on both sides thereof are fixed by being pinched by the microneedle puncture instrument. Accordingly, the microneedle can be more easily held punctured into the skin.

The above microneedle puncture instrument may further include a support shaft that extends in the array direction, wherein the pinch section may include: a first pinch section supported by a first shaft portion which is part of the support shaft, the first pinch section including a first upper portion, and a first lower portion located at a position different from the first upper portion in the pinch direction, the first upper portion and the first lower portion cooperating with each other to pinch the skin; and a second pinch section supported by a second shaft portion which is part of the support shaft, the second pinch section including a second upper portion, and a second lower portion located at a position different from the second upper portion in the pinch direction, the second upper portion and the second lower portion cooperating with each other to pinch the skin, the first pinch element may include the first shaft portion and the first pinch section, and the second pinch element may include the second shaft portion and the second pinch section.

With this configuration, the first pinch element and the second pinch element are supported by a single shaft of the support shaft. Accordingly, compared with the configuration in which the first pinch element and the second pinch element are separately supported by different support shafts, the skin which extends in a substantially two-dimensional plane such as upper arm and forearm can be more easily pinched by the first pinch element and the second pinch element.

In the above microneedle puncture instrument, the puncture section may include: a third shaft portion which is part of the support shaft located between the first shaft portion and the second shaft portion in the array direction; an upper puncture portion supported by the third shaft portion and including the support portion; and a lower puncture portion located at a position different from the upper puncture portion in the pinch direction, and the upper puncture portion and the lower puncture portion may cooperate with each other to pinch the skin.

With this configuration, the first pinch element, the second pinch element, and the puncture section are supported by a single shaft of the support shaft. Accordingly, compared with a configuration in which these are separately supported by different support shafts, fixation and puncture of the skin which extends in a substantially two-dimensional plane are facilitated.

In the above microneedle puncture instrument, the puncture section may be connected to the pinch section at a position between the first pinch element and the second pinch element in the array direction.

With this configuration, since the pinch section and the puncture section are connected to each other, the puncture section can be readily held at a predetermined position in the array direction between the first pinch element and the second pinch element, compared with the configuration in which the pinch section and the puncture section are separately provided. Accordingly, variation in the puncture state of the microneedle into the skin due to variation in position of the puncture section in the array direction among a plurality of microneedle puncture instruments can be reduced.

The above microneedle puncture instrument may further include: three upper portions arrayed in the array direction; and a lower portion extending in the array direction and located at a position different from all the upper portions in the pinch direction, the lower portion having a size overlapping with all the upper portions in the array direction when viewed in the pinch direction, wherein the first pinch element, the second pinch element, and the puncture section each have the individual upper portions, the upper portion of the puncture section include the support portion, and the pinch section and the puncture section share the lower portion.

With this configuration, since the pinch section and the puncture section share a single lower member which extends in the array direction, the pinch section may pinch the skin to thereby support a site of the skin to be punctured by the microneedle by the lower member. Accordingly, the puncture section can puncture the microneedle into a site supported by the lower member, which facilitates puncture of the skin by the microneedle.

In order to address the above problem, another aspect of the invention includes: a pinch section configured to pinch the skin in a pinch direction, the pinch section including an upper pinch portion, and a lower pinch portion located at a position different from the upper pinch portion in the pinch direction; and a puncture section configured to puncture the skin while pinching the skin in the pinch direction, the puncture section including an upper puncture portion which includes a microneedle for puncturing the skin and a support portion that supports the microneedle, and a lower puncture portion located at a position different from the upper puncture portion in the pinch direction, wherein the pinch section and the puncture section are arrayed in an array direction, which intersects with the pinch direction, the lower pinch portion and the lower puncture portion are included in a single lower portion extending in the array direction, the upper pinch portion and the upper puncture portion are located to face a same side of the lower portion, and the lower portion has a portion extending in the array direction from a position facing the upper puncture portion to a side opposite to that facing the upper pinch portion.

With this configuration, when the microneedle is punctured into the skin, the pinch section pinches the skin and thus the sites on both sides of a portion of the skin to be punctured by the microneedle in the array direction are supported by the lower portion. Accordingly, when the microneedle is punctured into the skin, deformation of the skin can be reduced since the skin is supported by the lower portion. Further, while the pinch section and the puncture section pinch the skin, a site which is in contact only with the lower portion, in addition to a site which is in contact with the upper pinch portion and a site which is in contact with the upper puncture portion, is fixed to a certain extent by the pinch section and the puncture section. Accordingly, the microneedle can be more easily held punctured into the skin.

Advantageous Effects of Invention

According to the present invention, a microneedle can be more easily held punctured into the skin.

DESCRIPTION OF REPRESENTATIVE EMBODIMENTS

Representative embodiments according to the present invention will hereafter be described below in detail and with reference to the drawings. The representative embodiments described below are merely examples of the present invention, and the design thereof could be appropriately changed by one skilled in the art.

With reference to FIGS. 1 to 8, an embodiment of a microneedle puncture instrument will be described. In the following description, a configuration of the microneedle puncture instrument and operation of the microneedle puncture instrument are described in sequence.

[Configuration of Microneedle Puncture Instrument]

Figure 1:
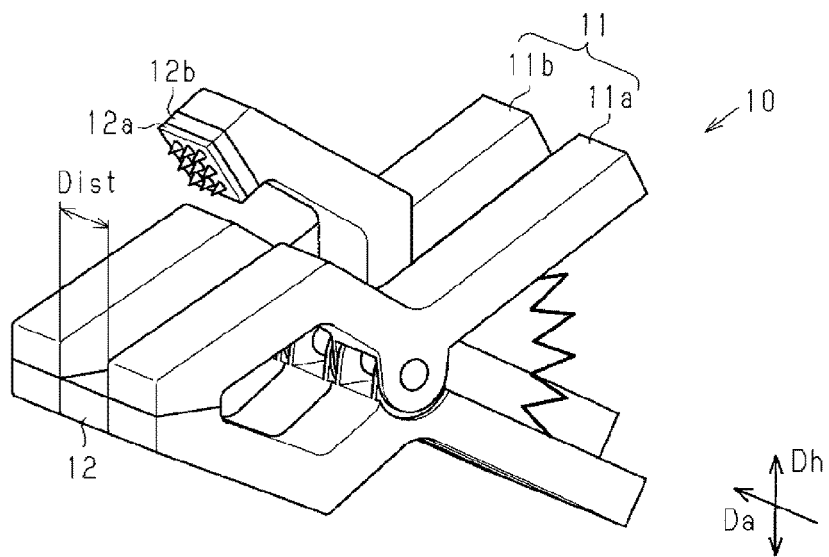
FIG. 1 is a perspective view illustrating a perspective structure according to an embodiment of a microneedle puncture instrument.
Figure 2:
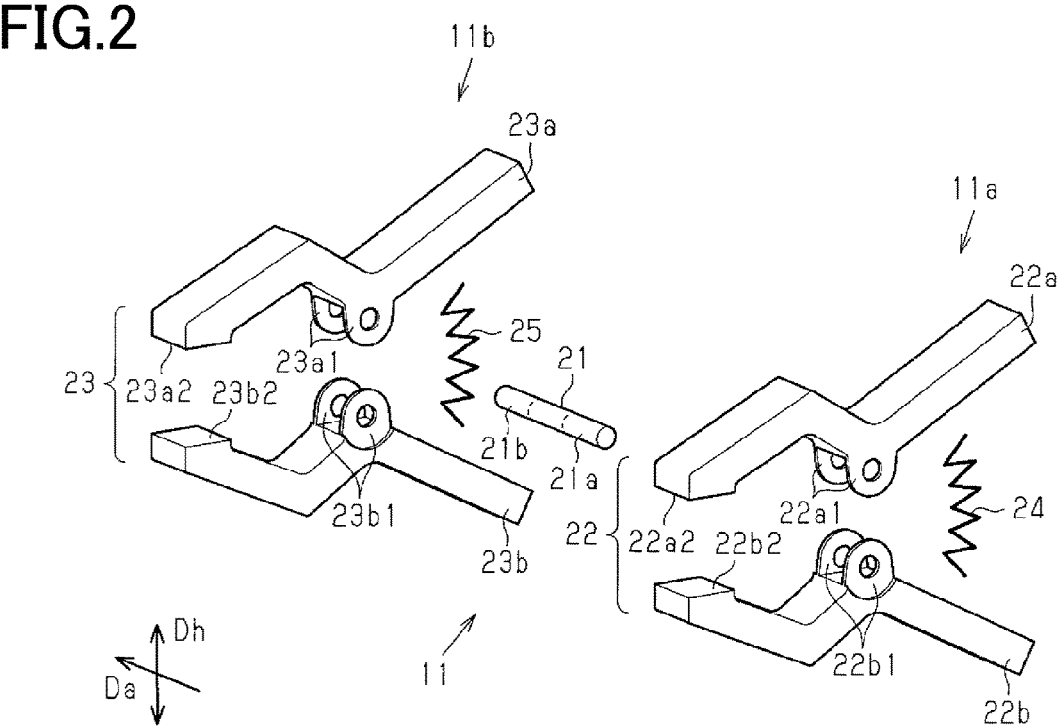
FIG. 2 is an exploded perspective view illustrating an exploded perspective structure of a pinch section according to an embodiment.
Figure 3:
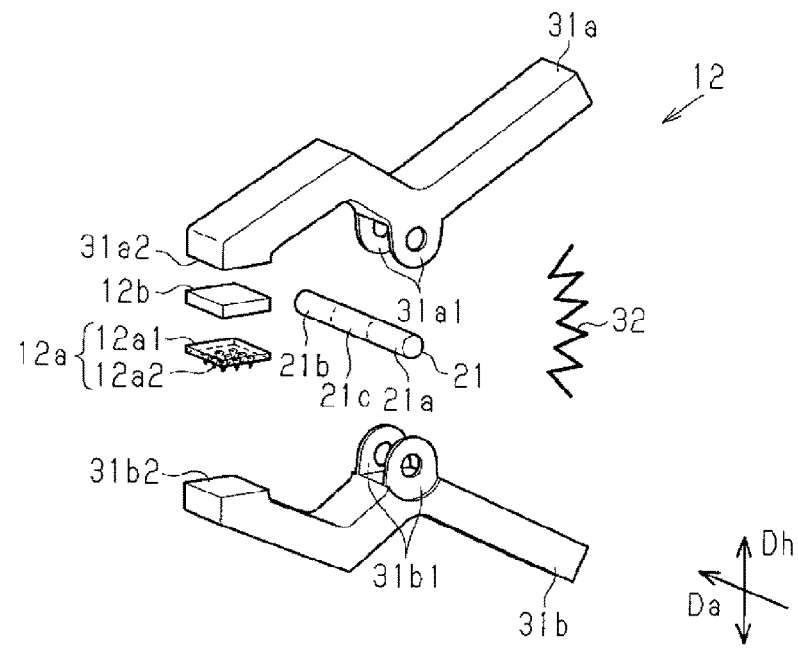
FIG. 3 is an exploded perspective view illustrating an exploded perspective structure of a puncture section according to an embodiment.

With reference to FIGS. 1 to 3, a configuration of microneedle puncture instrument will now be described.

As shown in FIG. 1, a microneedle puncture instrument 10 includes a pinch section 11 and a puncture section 12. The pinch section 11 is also called a pinch structure or a pinch assembly. The puncture section 12 is also called a puncture structure or a puncture assembly.

The pinch section 11 includes a first pinch element 11a and a second pinch element 11b, which are arrayed in an array direction Da, and individually pinch the skin in a pinch direction Dh, which is a direction intersecting with the array direction Da. The first pinch element 11a and the second pinch element 11b are connected to each other with a distance Dist between the first pinch element 11a and the second pinch element 11b being maintained within a predetermined range.

The puncture section 12 is configured to puncture the skin between the first pinch element 11a and the second pinch element 11b in the array direction Da while pinching the skin in the pinch direction Dh. The puncture section 12 includes a microneedle 12a for puncturing the skin, and a support portion 12b for supporting the microneedle 12a. A plane containing the array direction Da and a plane containing the pinch direction Dh intersect with each other. In the present embodiment, these planes are perpendicular to each other.

The microneedle puncture instrument 10 includes the first pinch element 11a, the puncture section 12, and the second pinch element 11b. The first pinch element 11a, the puncture section 12, and the second pinch element 11b are arrayed in sequence in a single direction, which is the array direction Da. The first pinch element 11a, the puncture section 12, and the second pinch element 11b are connected to each other.

Since the pinch section 11 and the puncture section 12 are connected to each other, the puncture section 12 can be readily held at a predetermined position in the array direction Da between the first pinch element 11a and the second pinch element 11b, compared with the configuration in which the pinch section and the puncture section are separately provided. Accordingly, variation in position of the puncture section 12 in the array direction Da among a plurality of different microneedle puncture instruments 10 can be reduced, and thus variation in the puncture state of the microneedle 12a into the skin can be reduced.

The first pinch element 11a, the second pinch element 11b, and the puncture section 12 each pinch the skin which is a puncture target of the microneedle 12a. A direction in which the first pinch element 11a, the second pinch element 11b, and the puncture section 12 pinch the skin is the pinch direction Dh. The pinch direction Dh is a direction in which a first portion in contact with the skin, the skin, and a second member in contact with the skin are arrayed in sequence in each of the first pinch element 11a, the second pinch element 11b, and the puncture section 12. In other words, the pinch direction Dh is a direction in which two portions which are in contact with the skin pinch the skin in each of the first pinch element 11a, the second pinch element 11b, and the puncture section 12.

The distance Dist between the first pinch element 11a and the second pinch element 11b is a distance between the first pinch element 11a and the second pinch element 11b in the array direction Da. Although the distance Dist is held at a predetermined distance, the distance Dist may have a predetermined range. In other words, the microneedle puncture instrument 10 can be configured to vary the distance between the first pinch element 11a and the second pinch element 11b in the array direction Da.

FIG. 2 is a view illustrating an exploded perspective structure of the members constituting the pinch section 11 of the microneedle puncture instrument 10.

As shown in FIG. 2, the microneedle puncture instrument 10 includes the support shaft 21 extending in the array direction Da, and the pinch section 11 includes a first pinch section 22 supported by the support shaft 21 and a second pinch section 23, which is also supported by the support shaft 21.

The first pinch section 22 includes a first upper portion and a first lower portion located at a position different from the first upper portion in the pinch direction Dh. The first pinch section 22 pinches the skin by using the first upper portion and the first lower portion. The second pinch section 23 includes a second upper portion and a second lower portion located at a position different from the second upper portion in the pinch direction Dh. The second pinch section 23 pinches the skin by using the second upper portion and the second lower portion.

In the pinch section 11, the first pinch element 11a described above includes a first shaft portion 21a, which is a portion of the support shaft 21, and the first pinch section 22, while the second pinch element 11b described above includes a second shaft portion 21b, which is a portion of the support shaft 21 and different from the first shaft portion 21a, and the second pinch section 23.

More preferably, the first pinch section 22 of the first pinch element 11a is composed of a first upper member 22a, which is an example of the first upper portion, and a first lower member 22b, which is an example of the first lower portion. A direction in which the first upper member 22a and the first lower member 22b are arrayed is the pinch direction Dh, and the first upper member 22*a* and the first lower member 22*b* are located in different positions in the pinch direction Dh.

The first upper member 22*a* has a fold line-shape extending in a direction intersecting with the array direction Da. That is, the first upper member 22*a* has a shape extending in a direction intersecting with the array direction Da, in a plane parallel with the plane containing the array direction Da. The first upper member 22*a* has upper supported pieces 22*a*1 disposed in the middle of the longitudinal length of the first upper member 22*a* and on both sides thereof in the array direction Da such that the upper supported pieces 22*a*1 are supported by the support shaft 21. The upper supported pieces 22*a*1 are supported by the support shaft 21, allowing for rotation of the first upper member 22*a* about the support shaft 21, which is taken as a rotation shaft.

The first lower member 22*b*, as with the first upper member 22*a*, has a fold line-shape extending in a direction intersecting with the array direction Da. That is, the first lower member 22*b* has a shape extending in a direction intersecting with the array direction Da, in a plane parallel with the plane containing the array direction Da. The first lower member 22*b* has lower supported pieces 22*b*1 disposed in the middle of the longitudinal length of the first lower member 22*b* and on both sides thereof in the array direction Da such that the lower supported pieces 22*b*1 are supported by the support shaft 21. The lower supported pieces 22*b*1 are fixed to the support shaft 21 so that the first lower member 22*b* does not rotate in the circumferential direction of the support shaft 21. The first lower member 22*b* has the shape corresponding to the first upper member 22*a*.

One end of the first upper member 22*a* is an upper pinch end 22*a*2, and one end of the first lower member 22*b*, facing the upper pinch end 22*a*2 in the pinch direction Dh, is a lower pinch end 22*b*2. An area of the lower pinch end 22*b*2 is the same as that of the upper pinch end 22*a*2. However, an area of the lower pinch end 22*b*2 and an area of the upper pinch end 22*a*2 may be different from each other.

The first pinch element 11*a* further includes a first bias member 24. The first bias member 24 extends in the pinch direction Dh such that one end of the first bias member 24 is connected to the first upper member 22*a* and the other end is connected to the first lower member 22*b*. When the first pinch element 11*a* is assembled, that is, the first upper member 22*a* and the first lower member 22*b* are supported by the first shaft portion 21*a* of the support shaft 21, the first bias member 24 biases the first upper member 22*a* in a direction that causes the upper pinch end 22*a*2 and the lower pinch end 22*b*2 to be in contact with each other.

Accordingly, when force is not applied to the first bias member 24, the first pinch element 11*a* is closed, and when force is applied to the first bias member 24 in a direction in which the length of the first bias member 24 is shortened, the first pinch element 11*a* is open. In other words, when force is not applied to the first bias member 24, the upper pinch end 22*a*2 and the lower pinch end 22*b*2 are in contact with each other, and when force is applied to the first bias member 24 in a direction in which the length of the first bias member 24 is shortened, the upper pinch end 22*a*2 and the lower pinch end 22*b*2 are separated from each other.

The second pinch section 23 of the second pinch element 11*b* is composed of a second upper member 23*a*, which is an example of the second upper portion, and a second lower member 23*b*, which is an example of the second lower portion. The second upper member 23*a* and the second lower member 23*b* are located in different positions in the pinch direction Dh. When the microneedle puncture instrument 10 is assembled, the position of the second upper member 23*a* is the same as the position of the first upper member 22*a*, and the position of the second lower member 23*b* is the same as the position of the first lower member 22*b* in the pinch direction Dh.

The second upper member 23*a*, as with the first upper member 22*a*, has a fold line-shape extending in a direction intersecting with the array direction Da. That is, the second upper member 23*a* has a shape extending in a direction intersecting with the array direction Da, in a plane parallel with the plane containing the array direction Da. The second upper member 23*a* has upper supported pieces 23*a*1 disposed in the middle of the longitudinal length of the second upper member 23*a* and on both sides thereof in the array direction Da such that the upper supported pieces 23*a*1 are supported by the support shaft 21. The upper supported pieces 23*a*1 are supported by the support shaft 21, allowing for rotation of the second upper member 23*a* about the support shaft 21, which is taken as a rotation shaft.

The second lower member 23*b*, as with the second upper member 23*a*, has a fold line-shape extending in a direction intersecting with the array direction Da. That is, the second lower member 23*b* has a shape extending in a direction intersecting with the array direction Da, in a plane parallel with the plane containing the array direction Da. The second lower member 23*b* has lower supported pieces 23*b*1 disposed in the middle of the longitudinal length of the second lower member 23*b* and on both sides thereof in the array direction Da such that the lower supported pieces 23*b*1 are supported by the support shaft 21. The lower supported pieces 23*b*1 are fixed to the support shaft 21 so that the second lower member 23*b* does not rotate in the circumferential direction of the support shaft 21. The second lower member 23*b* has the shape corresponding to the second upper member 23*a*, and also corresponding to first upper member 22*a*.

One end of the second upper member 23*a* is an upper pinch end 23*a*2, and one end of the second lower member 23*b*, facing the upper pinch end 23*a*2 in the pinch direction Dh, is a lower pinch end 23*b*2. An area of the lower pinch end 23*b*2 is the same as that of the upper pinch end 23*a*2. However, an area of the lower pinch end 23*b*2 and an area of the upper pinch end 23*a*2 may be different from each other.

The second pinch element 11*b* further includes a second bias member 25. The second bias member 25 extends in the pinch direction Dh such that one end of the second bias member 25 is connected to the second upper member 23*a* and the other end is connected to the second lower member 23*b*. When the second pinch element 11*b* is assembled, that is, the second upper member 23*a* and the second lower member 23*b* are supported by the second shaft portion 21*b* of the support shaft 21, the second bias member 25 biases the second upper member 23*a* in a direction that causes the upper pinch end 23*a*2 and the lower pinch end 23*b*2 to be in contact with each other.

Accordingly, when force is not applied to the second bias member 25, the second pinch element 11*b* is closed, and when force is applied to the second bias member 25 in a direction in which the length of the second bias member 25 is shortened, the second pinch element 11*b* is open. In other words, when force is not applied to the second bias member 25, the upper pinch end 23*a*2 and the lower pinch end 23*b*2 are in contact with each other, and when force is applied to the second bias member 25 in a direction in which the length of the second bias member 25 is shortened, the upper pinch end 23a2 and the lower pinch end 23b2 are separated from each other.

Materials for forming the pinch section 11 include resins such as polycarbonate, polypropylene, polystyrene, and polyethylene. However, the materials for forming the pinch section 11 are not limited to these resin materials. Materials for forming the pinch section 11 include resin materials other than those listed above, and may also include metal materials, and inorganic materials such as ceramics and glasses. Further, the materials for forming the pinch section 11 may also include composite materials of these materials.

FIG. 3 is a view illustrating an exploded perspective structure of the members constituting the puncture section 12 of the microneedle puncture instrument 10.

As shown in FIG. 3, the puncture section 12 includes a third shaft portion 21c, which is a portion of the support shaft 21 located between the first shaft portion 21a and the second shaft portion 21b in the array direction Da. Further, the puncture section 12 includes an upper puncture portion supported by the third shaft portion 21c and having the support portion 12b, and a lower puncture portion located at a position different from the upper puncture portion in the pinch direction Dh. In the puncture section 12, the upper puncture portion cooperates with the lower puncture portion to pinch the skin.

More specifically, the puncture section 12 includes an upper puncture member 31a and a lower puncture member 31b, and the upper puncture member 31a and the lower puncture member 31b are located in different positions in the pinch direction Dh. The upper puncture member 31a together with the support portion 12b is an example of the upper puncture portion, and the lower puncture member 31b is an example of the lower puncture portion. When the microneedle puncture instrument 10 is assembled, the position of the upper puncture member 31a is the same as the positions of first upper member 22a and the second upper member 23a, and the position of the lower puncture member 31b is the same as the positions of the first lower member 22b and the second lower member 23b in the pinch direction Dh.

The upper puncture member 31a has a fold line-shape extending in a direction intersecting with the array direction Da. That is, the upper puncture member 31a has a shape extending in a direction intersecting with the array direction Da, in a plane parallel with the plane containing the array direction Da. The upper puncture member 31a has upper supported pieces 31a1 disposed in the middle of the longitudinal length of the upper puncture member 31a and on both sides thereof in the array direction Da such that the upper supported pieces 31a1 are supported by the support shaft 21. The upper supported pieces 31a1 are supported by the support shaft 21, allowing for rotation of the upper puncture member 31a about the support shaft 21, which is taken as a rotation shaft.

The lower puncture member 31b, as with the upper puncture member 31a, has a fold line-shape extending in a direction intersecting with the array direction Da. That is, the lower puncture member 31b has a shape extending in a direction intersecting with the array direction Da, in a plane parallel with the plane containing the array direction Da. The lower puncture member 31b has lower supported pieces 31b1 disposed in the middle of the longitudinal length of the lower puncture member 31b and on both sides thereof in the array direction Da such that the lower supported pieces 31b1 are supported by the support shaft 21. The lower supported pieces 31b1 are fixed to the support shaft 21 so that the lower puncture member 31b does not rotate in the circumferential direction of the support shaft 21.

One end of the upper puncture member 31a is an upper puncture end 31a2, and one end of the lower puncture member 31b, facing the upper puncture end 31a2 in the pinch direction Dh, is a lower puncture end 31b2. An area of the lower puncture end 31b2 is the same as that of the upper puncture end 31a2. However, an area of the lower puncture end 31b2 may be larger than that of the upper puncture end 31a2.

The microneedle 12a includes a plate-shaped base 12a1, and a plurality of projections 12a2 extending from one surface of the base 12a1. Although the microneedle 12a includes a plurality of projections 12a2, it may include only one projection 12a2. Materials for forming the microneedle 12a are preferably biocompatible materials. For example, materials known in the art can be used as the biocompatible material. Examples of the biocompatible material include alginates, curdlan, chitin, chitosan, glucomannan, polymalic acid, collagen, collagen peptide, hydroxypropyl cellulose, gelatin, stainless steel, silicon, titanium, silicone resin, polylactic acid, polyglycolic acid and polyethylene. However, the biocompatible materials are not limited to these materials.

The microneedle 12a may include a drug. The administration method using the microneedle 12a is not specifically limited. For example, a drug may be applied on the surface of the projections 12a2 so that the drug is delivered into the skin when the projections 12a2 are punctured into the skin. Alternatively, a drug may be contained in the projections 12a2 so that the drug is delivered into the skin when the projections 12a2 are dissolved while being punctured into the skin. Further, a liquid drug may be applied on the skin before or after the projections 12a2 of the microneedle 12a are punctured into the skin so that the drug is delivered into the skin through the holes created by the projections 12a2.

Further, a liquid drug may be externally supplied to the microneedle 12a so that the drug is delivered into the skin via the projections 12a2. In this case, the microneedle 12a has a through hole which extends from the tip of the projection 12a2 to a surface of the base 12a1 on a side opposite to that on which the projection 12a2 is located. A drug is delivered into the skin through the through hole formed in the microneedle 12a. Further, when a drug is delivered into the skin through the through hole of the microneedle 12a, the upper puncture member 31a which supports the microneedle 12a, and the support portion 12b have a flow path that communicates with the through hole of the microneedle 12a so as to allow for distribution of a drug.

Moreover, a drug may be applied by combinations of these techniques. The projections 12a2 may be removed from the skin after they are punctured into the skin, or may be embedded in the skin when the projections 12a2 are made of a material soluble in the skin.

The type of the drug is not specifically limited as long as it works when administered into the skin, and may be, for example, physiologically active agents or cosmetic compositions having aesthetic effect. Moreover, the drug may include biologics. Biologics are drugs which use a raw material or material derived from cells or cell tissues of a human or an animal.

The support portion 12b that supports the microneedle 12a is disposed on the upper puncture end 31a2 of the upper puncture member 31a. The support portion 12b may be separately or integrally provided with the upper puncture member 31a.

The support portion 12*b*, separately provided from the upper puncture member 31*a*, may be an adhesive layer disposed on the upper puncture end 31*a*2, and a material for forming the adhesive layer may be either a pressure sensitive adhesive or an adhesive. The support portion 12*b*, thus adhered to the upper puncture member 31*a* and the microneedle 12*a*, can support the microneedle 12*a*.

On the other hand, the support portion 12*b*, integrally provided with the upper puncture member 31*a*, may be a recess formed by the uneven surface such that the microneedle 12*a* is fitted into the recess. The uneven surface may be any shape that serves as a plurality of threads. In the configuration in which the puncture section 12 includes the support portion 12*b*, a side surface of the base 12*a*1 in the microneedle 12*a*, perpendicular to the surface on which the projections 12*a*2 are located, may have unevenness serving as a plurality of threads that can be threaded with the support portion 12*b*.

An area of the base 12*a*1 of the microneedle 12*a* which can support the support portion 12*b* is equal to the area of the upper puncture end 31*a*2.

A portion of the upper puncture member 31*a* which includes the upper puncture end 31*a*2 is configured such that the projections 12*a*2 of the microneedle 12*a* are positioned extending in the tangent direction of an arc about the support shaft 21. In other words, the upper puncture member 31*a* is configured such that the projections 12*a*2 of the microneedle 12*a* mounted on the upper puncture end 31*a*2 extend in the normal direction to the skin of puncture target. A portion of the upper puncture member 31*a* which includes the upper puncture end 31*a*2 and extends from the upper supported pieces 31*a*1 to the upper puncture end 31*a*2 has substantially an L-shape. According to such a configuration, the skin can be punctured by the microneedle 12*a* in the approximately tangent direction of the skin. This facilitates puncture of the skin by the projections 12*a*2 of the microneedle 12*a*.

The puncture section 12 further includes a puncture bias member 32. The puncture bias member 32 extends in the pinch direction Dh such that one end of the puncture bias member 32 is connected to the upper puncture member 31*a* and the other end is connected to the lower puncture member 31*b*. When the puncture section 12 is assembled, that is, the upper puncture member 31*a* and the lower puncture member 31*b* are supported by the third shaft portion 21*c* of the support shaft 21, the puncture bias member 32 biases the upper puncture member 31*a* in a direction that causes the upper puncture end 31*a*2 and the lower puncture end 31*b*2 to approach each other.

Accordingly, when force is not applied to the puncture bias member 32, the puncture section 12 is closed, and when force is applied to the puncture bias member 32 in a direction in which the length of the puncture bias member 32 is shortened, the puncture section 12 is open. In other words, when force is not applied to the puncture bias member 32, the upper puncture end 31*a*2 and the lower puncture end 31*b*2 are in contact with each other, and when force is applied to the puncture bias member 32 in a direction in which the length of the puncture bias member 32 is shortened, the upper puncture end 31*a*2 and the lower puncture end 31*b*2 are separated from each other.

Materials for forming a portion of the puncture section 12 except for the microneedle 12*a* may include the same materials as those for the pinch section 11 described above. Further, in the case where the support portion 12*b* of the puncture section 12 is an adhesive layer, materials for forming the adhesive layer may include various types of pressure sensitive adhesives and adhesives as described above.

[Operation of Microneedle Puncture Instrument]

Figure 5:
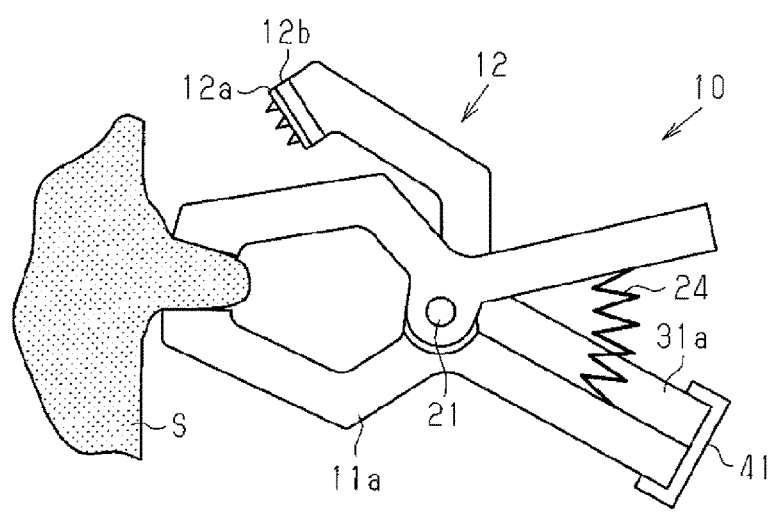
FIG. 5 is a diagram illustrating operation of an embodiment.
Figure 6:
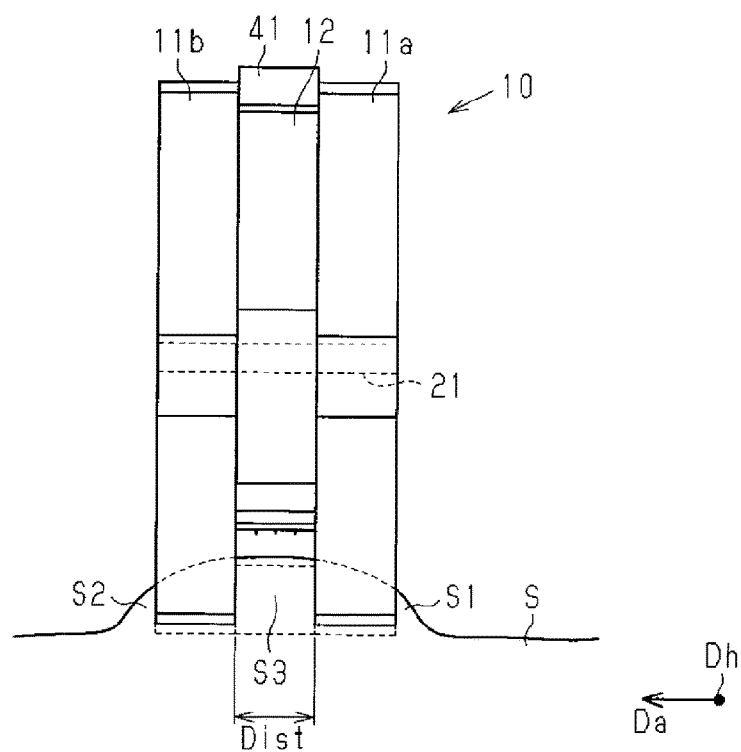
FIG. 6 is a diagram illustrating operation of an embodiment.
Figure 7:
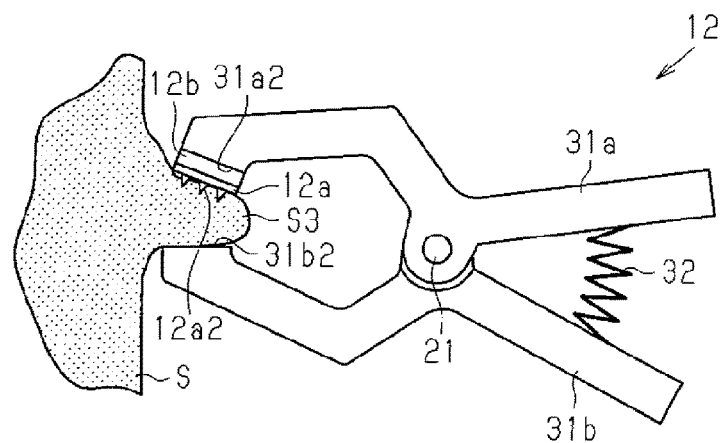
FIG. 7 is a diagram illustrating operation of an embodiment.

With reference to FIGS. 4 to 8, operation of the microneedle puncture instrument 10 will now be described. In FIG. 7, for the convenience of illustration and description, the first pinch element 11*a* is not illustrated.

Figure 4:
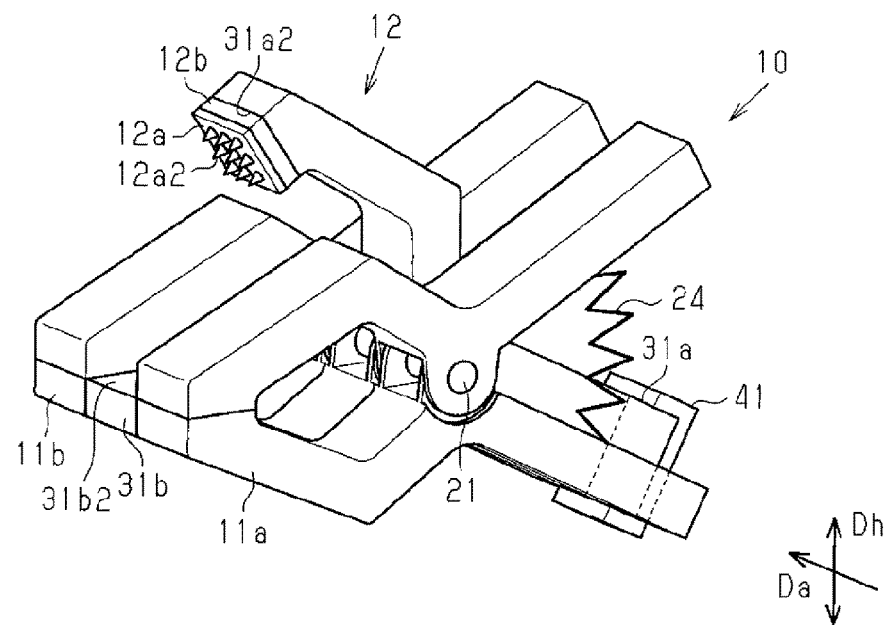
FIG. 4 is a diagram illustrating operation of an embodiment.

As shown in FIG. 4, in use of the microneedle puncture instrument 10 to puncture the skin, the microneedle 12*a* is first mounted on the support portion 12*b* of the puncture section 12. Here, it is preferred that a stopper 41 is mounted on the microneedle puncture instrument 10 when the puncture bias member 32 is compressed. The stopper 41 is preferably fixed while an end of the upper puncture member 31*a* on a side opposite to that having the upper puncture end 31*a*2 and an end of the lower puncture member 31*b* on a side opposite to that having the lower puncture end 31*b*2 are in contact with each other.

Although the puncture bias member 32 can be manually compressed in mounting of the microneedle 12*a*, a force applied to the puncture bias member 32 may be unintentionally reduced in the course of operation of mounting the microneedle 12*a*. This may cause the projections 12*a*2 of the microneedle 12*a* to be in contact with the lower puncture member 31*b* or the like, leading to deformation of the projections 12*a*2. Accordingly, it is preferred that the stopper 41 is used to apply a force to the puncture bias member 32 in a direction that compresses the puncture bias member 32.

Then, as shown in FIG. 5, a portion of a skin S is pinched by the first pinch element 11*a*, and another portion of the skin S, which is different from the portion pinched by the first pinch element 11*a*, is pinched by the second pinch element 11*b*. Here, an operation of pinching the skin S by the first pinch element 11*a* and an operation of pinching the skin S by the second pinch element 11*b* may be performed at the same or different timings.

As shown in FIG. 6, the first pinch element 11*a* pinches a first portion S1 of the skin S, and the second pinch element 11*b* pinches a second portion S2 of the skin S. Accordingly, the first portion S1 of the skin S and the second portion S2 of the skin S are fixed, and thus the skin S is fixed by the first pinch element 11*a* and the second pinch element 11*b*.

The first pinch element 11*a* and the second pinch element 11*b* arrayed in the array direction Da. Further, the distance Dist between the first pinch element 11*a* and the second pinch element 11*b* is a size that allows the third portion S3 between the first portion S1 and the second portion S2 of the skin is fixed to a certain extent when the first portion S1 and the second portion S2 are fixed.

As shown in FIG. 7, when the stopper 41 is removed from the puncture section 12, a force in the direction that compresses the puncture bias member 32 is released. Thus, the puncture bias member 32 biases the upper puncture member 31*a* in a direction that causes the upper puncture end 31*a*2 and the lower puncture end 31*b*2 approaches each other. Accordingly, while the puncture section 12 pinches the third portion S3 of the skin S, the projections 12*a*2 of the microneedle 12*a* punctures the skin S.

Since the area of the lower puncture end 31*b*2 is the same as that of the base 12*a*1 of the microneedle 12*a*, the area of the third portion S3 pinched between the lower puncture end 31*b*2 and the microneedle 12*a* is not likely to be smaller than the area of the base 12*a*1 of the microneedle 12*a*. Accordingly, all the projections 12*a*2 of the microneedle 12*a* are likely to be punctured into the third portion S3 of the skin S.

Figure 8:
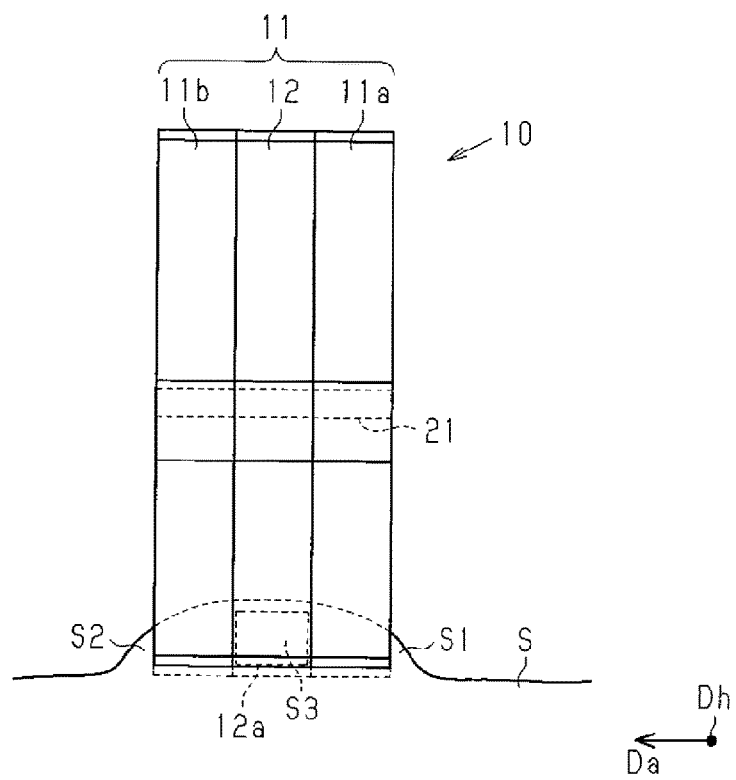
FIG. 8 is a diagram illustrating operation of an embodiment.

As shown in FIG. 8, when the microneedle 12a is punctured into the skin S, the pinch section 11 pinches the first portion S1 and the second portion S2, which are sites on both sides of the third portion S3, which is a site of the skin S to be punctured by the microneedle 12a, so that the respective portions are fixed. Moreover, since the puncture section 12 having the microneedle 12a also pinches the third portion S3 located between the sites pinched by the pinch section 11 when the microneedle 12a is punctured into the skin S, the third portion S3 of the skin S, which is to be punctured by the microneedle 12a is also fixed.

As described above, when and while the microneedle 12a is punctured into the skin S, a site of the skin S to be punctured by the microneedle 12a and sites on both sides thereof are fixed by being pinched by the microneedle puncture instrument 10. Accordingly, the microneedle 12a can be more easily held punctured into the skin S.

Both the first pinch element 11a and the second pinch element 11b are supported by a single shaft of the support shaft 21. Accordingly, compared with the configuration in which the first pinch element 11a and the second pinch element 11b are separately supported by different support shafts, the skin S which extends in a substantially two-dimensional plane such as upper arm and forearm can be more easily pinched by the first pinch element 11a and the second pinch element 11b. Moreover, since the puncture section 12 is also supported by the support shaft 21, fixation and puncture of the skin S which extends in a substantially two-dimensional plane are facilitated.

As described above, according to an embodiment of the microneedle puncture instrument, the following effects can be obtained.

(1) As described above, when and while the microneedle 12a is punctured into the skin S, a site of the skin S to be punctured by the microneedle 12a and sites on both sides thereof are fixed by being pinched by the microneedle puncture instrument 10. Accordingly, the microneedle 12a can be more easily held punctured into the skin S.

(2) Since both the first pinch element 11a and the second pinch element 11b are supported by the support shaft 21, the skin S which extends in a substantially two-dimensional plane can be more easily pinched by the first pinch element 11a and the second pinch element 11b.

(3) Since the first pinch element 11a, the second pinch element 11b, and the puncture section 12 are supported by the common support shaft 21, fixation and puncture of the skin S which extends in a substantially two-dimensional plane are facilitated.

(4) Since the pinch section 11 and the puncture section 12 are connected to each other, the puncture section 12 can be readily held at a predetermined position in the array direction Da between the first pinch element 11a and the second pinch element 11b, compared with the configuration in which the pinch section and the puncture section are separately provided. Accordingly, variation in the puncture state of the microneedle 12a into the skin S due to variation in position of the puncture section 12 in the array direction Da among a plurality of microneedle puncture instruments 10 can be reduced.

Furthermore, the aforementioned embodiments can be appropriately modified as described below.

First Modified Example

Figure 9:
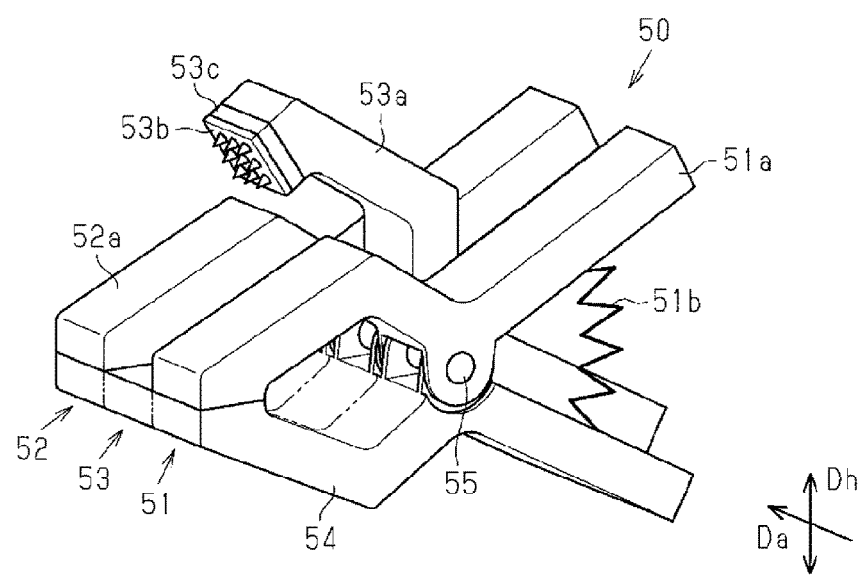
FIG. 9 is a perspective view illustrating a perspective structure of a first modified example.

With reference to FIG. 9, a first modified example of the microneedle puncture instrument will now be described.

The microneedle puncture instrument is not limited to a configuration in which the first pinch element 11a, the second pinch element 11b, and the puncture section 12 each have separate lower members, but may have a configuration in which the pinch section 11 and the puncture section 12 have a single common lower member.

That is, as shown in FIG. 9, a microneedle puncture instrument 50 includes three upper portions arrayed in the array direction Da, and a lower portion which extends in the array direction Da. The lower portion is located at a position different from all the upper portions in the pinch direction Dh, and has a size overlapping with all the upper portions in the array direction Da when viewed in the pinch direction Dh. A first pinch element 51, a second pinch element 52, and a puncture section 53 have individual upper portions. The upper portion of the puncture section includes the support portion, and the pinch section and the puncture section share the lower portion.

More specifically, the microneedle puncture instrument 50 includes three upper members arrayed in the array direction Da. The three upper members are a first upper member 51a included in the first pinch element 51, a second upper member 52a included in the second pinch element 52, and an upper puncture member 53a included in the puncture section 53. Of the three upper members, the upper puncture member 53a includes a support portion 53c that supports the microneedle 53b.

The first upper member 51a and the second upper member 52a are each an example of the upper portion, and the upper puncture member 53a and the support portion 53c constitute an example of the upper portion.

The microneedle puncture instrument 50 includes a single lower member 54, which is an example of the lower portion described above. The lower member 54 extends in the array direction Da, and is located at a position different from all the first upper member 51a, the second upper member 52a, and the upper puncture member 53a in the pinch direction Dh.

The lower member 54 has a size overlapping with all the first upper member 51a, the second upper member 52a, and the upper puncture member 53a in the array direction Da when viewed in the pinch direction Dh. In other words, in the array direction Da, the width of the lower member 54 is equal to the sum of the width of the first upper member 51a, the width of the second upper member 52a, and the width of the upper puncture member 53a. However, the width of the lower member 54 is larger than the sum of the width of the first upper member 51a, the width of the second upper member 52a, and the width of the upper puncture member 53a.

The first pinch element 51, the second pinch element 52, and the puncture section 53 share a single lower member 54. Accordingly, the first pinch element 51 pinches the skin by the first upper member 51a and part of the lower member 54, the second pinch element 52 pinches the skin by the second upper member 52a and part of the lower member 54, and the puncture section 53 pinches the skin by the upper puncture member 53a and part of the lower member 54.

The first pinch element 51 includes the first bias member 51b such that one end of the first bias member 51b is connected to the first upper member 51a and the other end is connected to the lower member 54. Although not shown in the figure, the second pinch element 52 includes a second bias member that is connected to the second upper member 52a and the lower member 54, and the puncture section 53 includes a puncture bias member that is connected to the upper puncture member 53a and the lower member 54.

The microneedle puncture instrument 50 includes a support shaft 55 extending in the array direction Da, and three upper members and the lower member 54 are supported by the support shaft 55.

Moreover, in the direction in which the lower member 54 extends, a portion of the lower member 54 extending from the support shaft 55 to an end facing the microneedle 53b may be separated into three portions as the aforementioned embodiment, or may be separated into two portions, or may be formed of a single portion.

According to this configuration, the following effects can be obtained.

(5) Since the first pinch element 51, the second pinch element 52, and the puncture section 53 share a single lower member 54 which extends in the array direction Da, the first pinch element 51 and the second pinch element 52 pinch the skin to thereby support a site of the skin to be punctured by the microneedle 53b by the lower member 54. Accordingly, the puncture section 53 can puncture the microneedle 53b into a site supported by the lower member 54, which facilitates puncture of the skin by the microneedle 53b.

Figure 11:
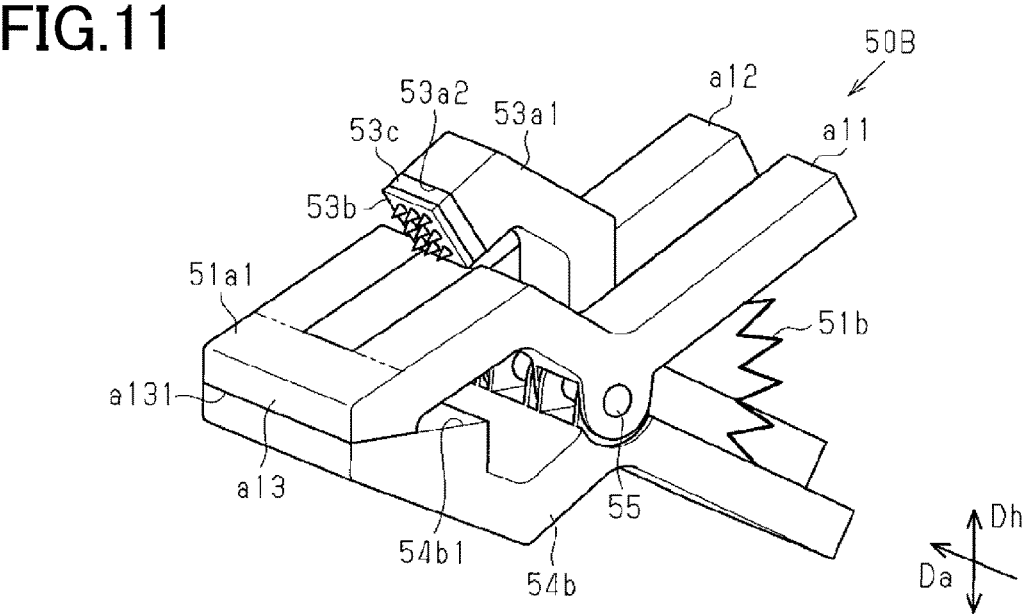
FIG. 11 is a perspective view illustrating a perspective structure of a second example, which is a further modification of the first modified example.
Figure 12:
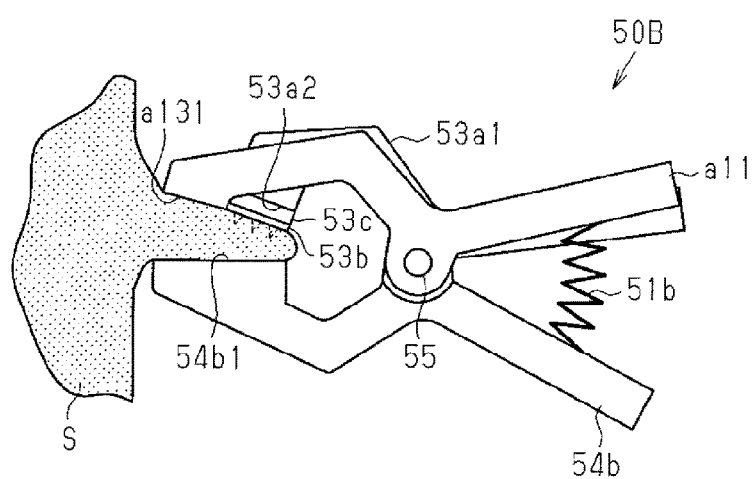
FIG. 12 is a diagram illustrating operation of the second example, which is a further modification of the first modified example.
Figure 13:
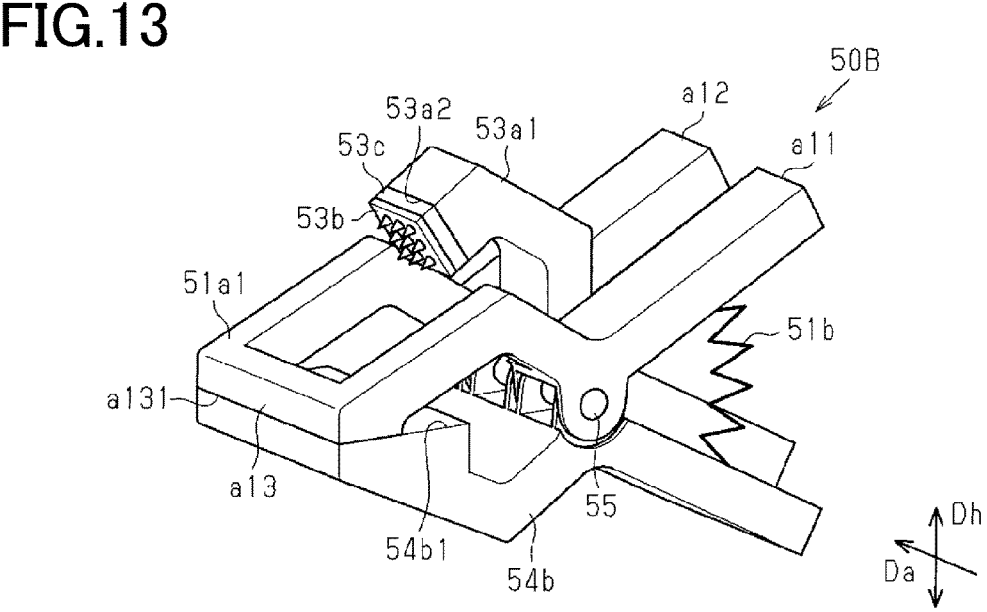
FIG. 13 is a perspective view illustrating a perspective structure of an example, which is a further modification of the second example.

The first modified example can be further modified as follows. In the following description, referring to FIG. 10, a first example, which is a further modification of the first modified example, will be described. Referring to FIGS. 11 and 12, a second example, which is a further modification of the first modified example, will be described. Referring to FIG. 13, a third example, which is a further modification of the first modified example, will be described.

First Example

Figure 10:
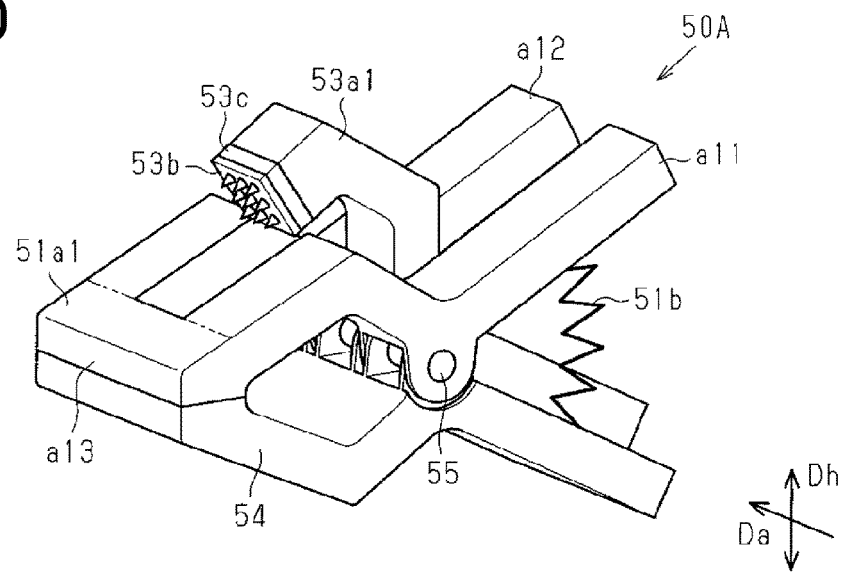
FIG. 10 is a perspective view illustrating a perspective structure of a first example, which is a further modification of the first modified example.

As shown in FIG. 10, a microneedle puncture instrument 50A may be configured to include a single upper pinch member 51a1 and a single upper puncture member 53a1. The upper pinch member 51a1 includes a first portion a11 and a second portion a12 arrayed in the array direction Da. The first portion a11 and the second portion a12 each have a fold line-shape extending in a direction intersecting with the array direction Da. That is, the first portion a11 and the second portion a12 each have a shape extending along a plane parallel with the plane containing the array direction Da. The upper pinch member 51a1 includes a third portion a13, which joins the first portion a11 and the second portion a12 at an end to be in contact with the skin which is a puncture target. The third portion a13 has a shape extending in the array direction Da, and faces an end of the lower member 54 which is to be in contact with the skin in the pinch direction Dh. A portion of the upper pinch member 51a1 extending from the support shaft 55 to an end on a side opposite to that having the first bias member 51b has a U-shape as viewed in the pinch direction Dh.

Further, the microneedle puncture instrument 50A includes the first bias member 51b and a second bias member, not shown in the figure. The first bias member 51b is connected to the first portion a11 and the lower member 54, and the second bias member includes the second portion a12 and the lower member 54.

The upper puncture member 53a1 is located between the first portion a11 and the second portion a12 in the array direction Da. The upper puncture member 53a1 has a shape extending in a direction parallel with the first portion a11 and the second portion a12. In the direction intersecting with the array direction Da, that is, in the direction in which the upper puncture member 53a1 extends, the third portion a13 of the upper pinch member 51a1 and the support portion 53c of the upper puncture member 53a1 are located in different positions. In other words, when a portion of the upper pinch member 51a1 which cooperates with the lower member 54 to pinch the skin is referred to as a distal end, and an end opposite to the distal end is referred to as a proximal end, the support portion 53c of the upper puncture member 53a1 is located offset from the third portion a13 of the upper pinch member 51a1 to the proximal end. Accordingly, the microneedle 53b supported by the support portion 53c is also located offset from the third portion a13 of the upper pinch member 51a1 to the proximal end.

In use of the microneedle puncture instrument 50A to puncture the skin, the skin is first pinched by the upper pinch member 51a1 and the lower member 54. Accordingly, a portion of the skin to be punctured by the microneedle 53b is surrounded by a U-shaped portion for fixation. Thus, a portion of the skin to be punctured by the microneedle 53b is fixed, facilitating puncture by the microneedle 53b.

Further, the upper pinch member 51a1 of the microneedle puncture instrument 50A and the upper puncture member 53a1 may be implemented in combination with the configuration of the aforementioned embodiment. That is, the microneedle puncture instrument 10 may include the upper pinch member 51a1 instead of the first upper member 22a and the second upper member 23a, and the upper puncture member 53a1 described above referring to FIG. 10 instead of the upper puncture member 31a.

Second Example

As shown in FIG. 11, an end of the lower member 54b to be in contact with the skin is a lower pinch end 54b1. The lower pinch end 54b1 faces an upper pinch end a131 of a third portion a13 of the upper pinch member 51a1 in the pinch direction Dh. An end of the upper puncture member 53a1 on which a support portion 53c is located is an upper puncture end 53a2. When viewed in the pinch direction Dh, the lower pinch end 54b1 has an area larger than an area of the upper pinch end a131, and the lower pinch end 54b1 has a size overlapping with both the upper pinch end a131 and the upper puncture end 53a2.

Since the size of the support portion 53c and the microneedle 53b supported by the support portion 53c are equal to the size of the upper puncture end 53a2, the lower pinch end 54b1 has a size overlapping with both the upper pinch end a131 and the microneedle 53b when viewed in the pinch direction Dh.

Accordingly, as shown in FIG. 12, in use of the microneedle puncture instrument 50B to puncture the skin, a portion of the skin S to be punctured is first pinched by the lower pinch end 54b1 and the upper pinch end a131. As described above, since the lower pinch end 54b1 is larger than the upper pinch end a131 as viewed in the pinch direction Dh, a portion of the skin S extending outside from the upper pinch end a131 is also fixed by the lower pinch end 54b1. Then, when the upper puncture end 53a2 of the upper puncture member 53a1 is brought close to the lower pinch end 54b1, the skin S is punctured by the microneedle 53b. Here, as described above, since the microneedle 53b and the lower pinch end 54b1 overlap with each other when viewed in the pinch direction Dh, a portion of the skin S extending outside from the upper puncture end 53a2 is pinched by the microneedle 53b and the lower pinch end 54b1.

Therefore, compared with a configuration in which the lower pinch end 54b1 and the upper pinch end a131 have the same size, puncture of the skin S by the microneedle 53b can be facilitated by an overlapping area between the lower pinch end 54b1 and the upper puncture end 53a2 which supports the microneedle 53b when viewed in the pinch direction Dh.

The second example can be further modified.

That is, a region defined by the first portion a11, the second portion a12, and the third portion a13 of the upper pinch member 51a1 may be larger than a region occupied by the upper puncture member 53a1 when viewed in the pinch direction Dh. In other words, a region occupied by the upper puncture member 53a1 may be smaller than a region defined by the upper pinch member 51a1 when viewed in the pinch direction Dh.

For example, as shown in FIG. 13, a portion of the first portion a11 extending from the support shaft 55 to the third portion a13 is thinner than a portion extending from the support shaft 55 to an end on a side opposite to that having the third portion a13. Here, in the portion of the first portion a11 extending from the support shaft 55 to the third portion a13, a surface which is closer to the upper puncture member 53a1 is depressed toward a surface of the first portion a11 facing away from the upper puncture member 53a1. Further, a portion of the second portion a12 extending from the support shaft 55 to the third portion a13 is thinner than a portion extending from the support shaft 55 to an end on a side opposite to that having the third portion a13. Here, in the portion of the second portion a12 extending from the support shaft 55 to the third portion a13, a surface which is closer to the upper puncture member 53a1 is depressed toward a surface of the second portion a12 facing away from the upper puncture member 53a1.

Further, the thickness of the third portion a13 in an extending direction of the upper pinch member 51a1 is designed such that a gap is formed between the third portion a13 and the upper puncture member 53a1 as viewed in the pinch direction Dh, when the microneedle 53b punctures the skin.

Accordingly, a region defined by the first portion a11, the second portion a12, and the third portion a13 of the upper pinch member 51a1 can be larger than a region occupied by the upper puncture member 53a1 when viewed in the pinch direction Dh.

Third Example

In a microneedle puncture instrument 50B of the second example, the upper pinch member 51a1 may be divided into two members.

Figure 14:
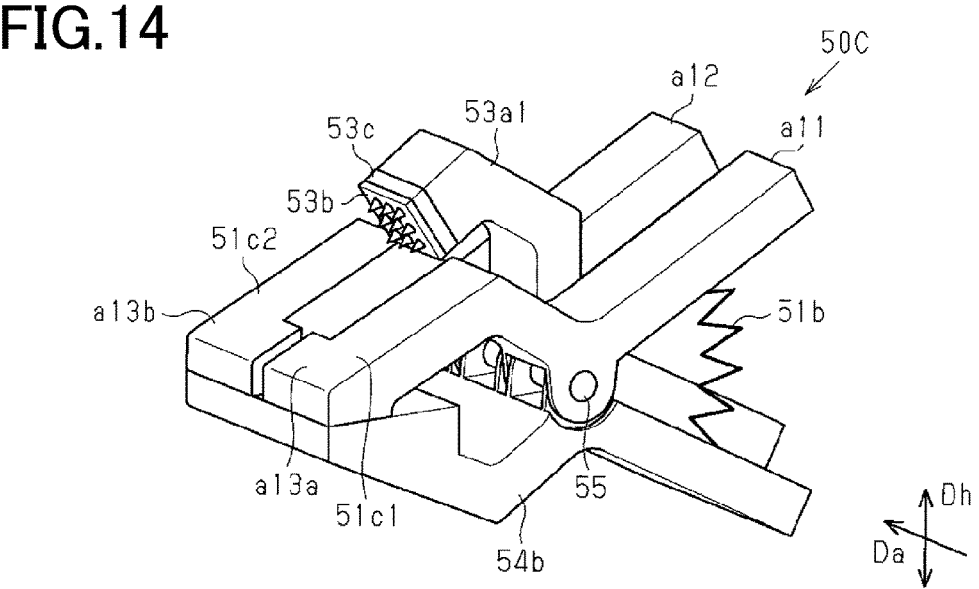
FIG. 14 is a perspective view illustrating a perspective structure of a third example, which is a further modification of the first modified example.

That is, as shown in FIG. 14, a microneedle puncture instrument 50C includes a first upper member 51c1 and a second upper member 51c2, and the upper puncture member 53a1 is located between the first upper member 51c1 and the second upper member 51c2 in the array direction Da. The first upper member 51c1 includes the first portion a11 and a first distal portion a13a. The first portion a11 has a shape extending in a direction intersecting with the array direction Da, and the first distal portion a13a has a shape extending from one end of the first portion a11 toward the second upper member 51c2 in the array direction Da. The second upper member 51c2 includes the second portion a12 and a second distal portion a13b. The second portion a12 has a shape extending in a direction intersecting with the array direction Da, and the second distal portion a13b has a shape extending from one end of the second portion a12 toward the first upper member 51c1 in the array direction Da. In the array direction Da, a gap is formed between the first distal portion a13a and the second distal portion a13b.

Such a configuration can still achieve an effect similar to the above second example.

Second Modified Example

Figure 15:
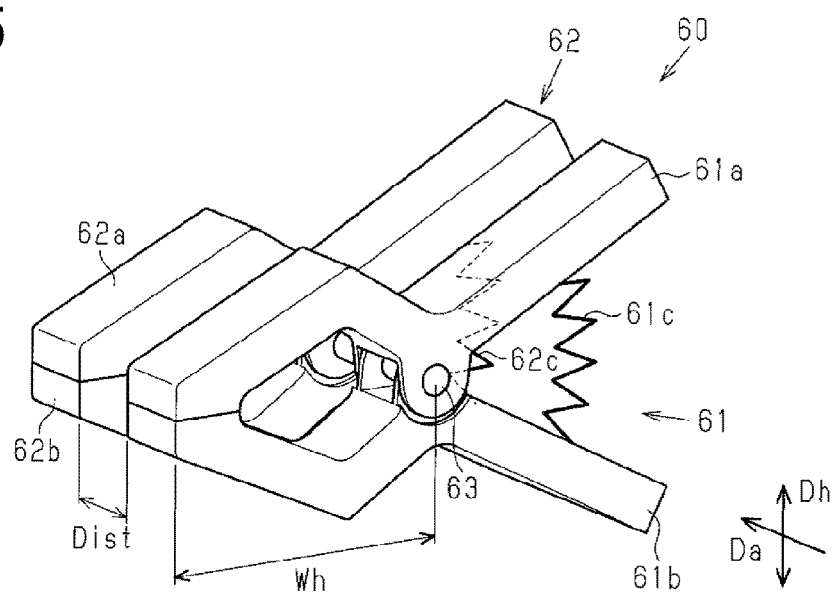
FIG. 15 is a perspective view illustrating a perspective structure of the pinch section according to a second modified example.
Figure 16:
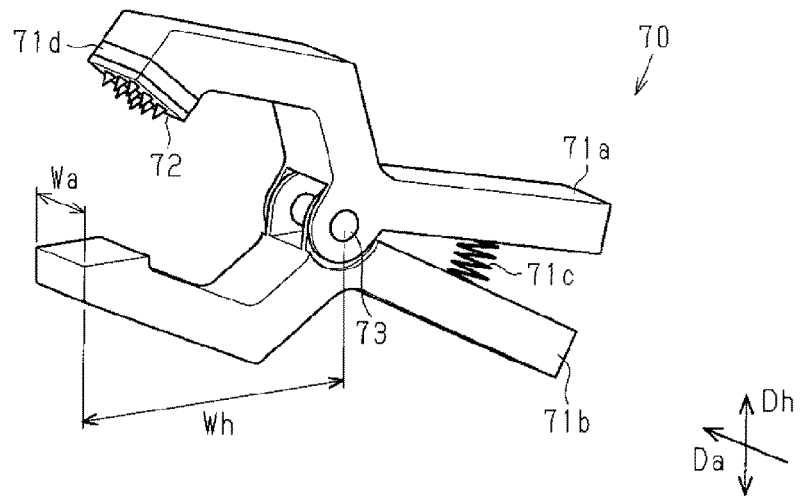
FIG. 16 is a perspective view illustrating a perspective structure of the puncture section according to the second modified example.

With reference to FIGS. 15 and 16, a second modified example of the microneedle puncture instrument will now be described.

The microneedle puncture instrument is not limited to a configuration in which the pinch section and the puncture section are connected to each other, but may have a configuration in which the pinch section and the puncture section are separated.

That is, as shown in FIG. 15, the pinch section 60 includes a first pinch element 61 and a second pinch element 62 arrayed in the array direction Da. The first pinch element 61 includes a first upper member 61a, a first lower member 61b, and a first bias member 61c that connects the first upper member 61a and the first lower member 61b. The second pinch element 62 includes a second upper member 62a, a second lower member 62b, and a second bias member 62c that connects the second upper member 62a and the second lower member 62b.

The pinch section 60 includes a support shaft 63 extending in the array direction Da, and the first upper member 61a and first lower member 61b are supported by the support shaft 63. The first pinch element 61 includes part of the support shaft 63. As with the first upper member 61a and the first lower member 61b, the second upper member 62a and the second lower member 62b are supported by the support shaft 63, and the second pinch element 62 includes part of the support shaft 63.

A distance between the first pinch element 61 and the second pinch element 62 in the array direction Da, in other words, a distance between the first upper member 61a and the second upper member 62a in the array direction Da is a distance Dist between the first pinch element 61 and the second pinch element 62.

On the other hand, in each of the first upper member 61a and the first lower member 61b, a distance along a radial direction of the support shaft 63 from the support shaft 63 to an end on a side opposite to that having the first bias member 61c is a pinch width Wh. Further, in each of the second upper member 62a and the second lower member 62b, a distance along a radial direction of the support shaft 63 from the support shaft 63 to an end on a side opposite to that having the second bias member 62c is also a pinch width Wh. The pinch width Wh of the first pinch element 61 is the same as the pinch width Wh of the second pinch element 62.

As shown in FIG. 16, a puncture section 70 includes an upper puncture member 71a, a lower puncture member 71b, a puncture bias member 71c that connects to the upper puncture member 71a and the lower puncture member 71b, and a support portion 71d, and a microneedle 72. The puncture section 70 includes a support shaft 73 extending in the array direction Da, and the upper puncture member 71a and the lower puncture member 71b are supported by the support shaft 73.

In the upper puncture member 71a and the lower puncture member 71b, a distance along the array direction Da is an array width Wa. The array width Wa is no more than the distance Dist between the first pinch element 61 and the second pinch element 62. On the other hand, in each of the upper puncture member 71a and the lower puncture member 71b, a distance along a radial direction of the support shaft 73 from the support shaft 73 to an end on a side opposite to that having the puncture bias member 71c is a pinch width Wh.

The pinch width Wh of the puncture section 70 is preferably no less than each of the pinch width Wh of the first pinch element 61 and the pinch width Wh of second pinch element 62.

According to the microneedle puncture instrument composed of the pinch section 60 and the puncture section 70, two sites of the skin adjacent in the array direction Da are first pinched by the pinch section 60. Then, while the puncture section 70 is located between the first pinch element 61 and the second pinch element 62 in the array direction Da, the skin is pinched by the puncture section 70 from a position farther from the skin with the support shaft 63 of the pinch section 60 positioned therebetween. Accordingly, the microneedle 72 can be punctured into the skin.

Thus, the puncture section 70 punctures the skin from a position farther from the skin with the support shaft 63 of the pinch section 60 positioned therebetween. As described above, the pinch width Wh of the puncture section 70 is preferably no less than each of the pinch width Wh of the first pinch element 61 and the pinch width Wh of the second pinch element 62. More preferably, the pinch width Wh of the puncture section 70 is larger than each of the pinch width Wh of the first pinch element 61 and the pinch width Wh of the second pinch element 62. Accordingly, the microneedle 72 can be more easily punctured into the skin.

In this configuration as well, an effect which is the same as that of the above (1) can be achieved.

The configuration of the puncture section of the microneedle puncture instrument according to the second modified example may be either of two configurations described below.

Figure 17:
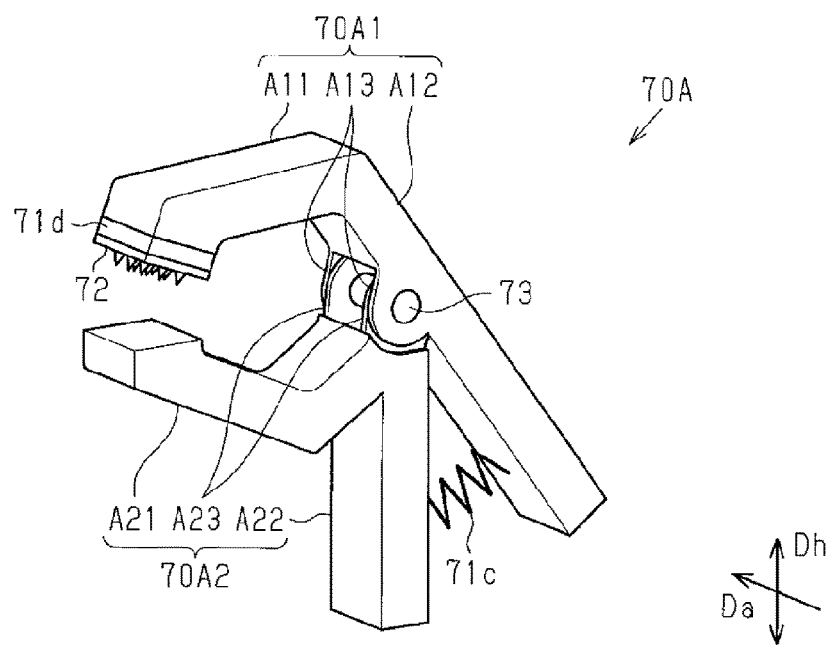
FIG. 17 is a perspective view illustrating a perspective structure of another puncture section according to the second modified example.

That is, as shown in FIG. 17, the puncture section 70A includes an upper puncture member 70A1 and a lower puncture member 70A2. The upper puncture member 70A1 includes a first portion A11 having a support portion 71d, and a second portion A12 which is bent from the first portion A11 and extends downward in the plane of the drawing. The second portion A12 includes upper supported pieces A13 disposed in the middle of the longitudinal length of the second portion A12 extending downward, and a portion of the second portion A12 extending from the upper supported pieces A13 to an end on a side opposite to that having the first portion A11 is a grip portion for a user of the puncture section 70A.

The lower puncture member 70A2 includes a first portion A21 and a second portion A22. The first portion A21 includes a portion that faces the support portion 71d in the pinch direction Dh when the puncture section 70A is closed. The second portion A22 has a straight shape which is bent from the first portion A21 and extends downward in the plane of the drawing. Lower supported pieces A23 are disposed between the first portion A21 and the second portion A22, and the second portion A22 has a shape extending from the lower supported pieces A23 in substantially the pinch direction Dh. The second portion A22 is a grip portion for a user of the puncture section 70A.

In such a configuration, when the skin pinched by the pinch section 60 is punctured by the microneedle 72, an extending direction of the second portion A12 of the upper puncture member 70A1 and an extending direction of the second portion A22 of the lower puncture member 70A2 intersect with an extending direction of the first pinch element 61 and the second pinch element 62. Accordingly, gripping of the puncture section 70A by a user is not likely to be disturbed by the first pinch element 61 and the second pinch element 62.

Figure 18:
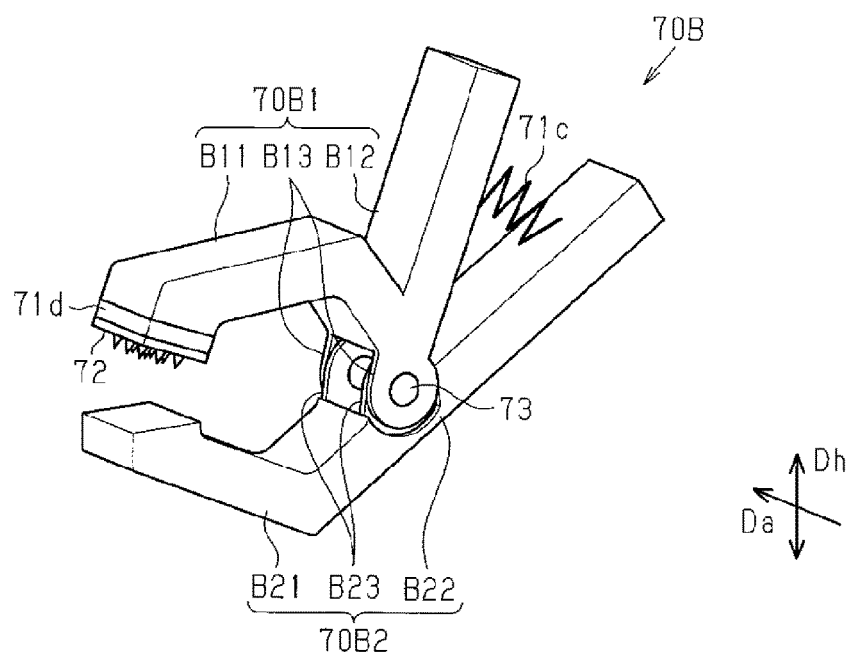
FIG. 18 is a perspective view illustrating a perspective structure of another puncture section according to the second modified example.

As shown in FIG. 18, a puncture section 70B includes an upper puncture member 70B1 and a lower puncture member 70B2. The upper puncture member 70B1 includes a first portion B11 having a support portion 71d, and a second portion B12 which is bent from the first portion B11 and extends upward in the plane of the drawing. Upper supported pieces B13 are disposed between the first portion B11 and the second portion B12, and the second portion B12 has a shape extending from the upper supported pieces B13 in substantially the pinch direction Dh. The second portion B12 is a grip portion for a user of the puncture section 70B.

The lower puncture member 70B2 includes a first portion B21 and a second portion B22. The first portion B21 includes a portion that faces the support portion 71d in the pinch direction Dh when the puncture section 70B is closed. The second portion B22 has a straight shape which is bent from the first portion B21 and extends upward in the plane of the drawing. The second portion B22 includes lower supported pieces B23 disposed in the middle of the longitudinal length of the second portion B22 extending upward in the plane of the drawing, and a portion of the second portion B22 extending from the lower supported pieces B23 to an end on a side opposite to that having the first portion B21 is a grip portion for a user of the puncture section 70B.

In such a configuration, as with the puncture section 70A described above, when the skin pinched by the pinch section 60 is punctured by the microneedle 72, an extending direction of the second portion B12 of the upper puncture member 70B1 and an extending direction of the second portion B22 of the lower puncture member 70B2 intersect with an extending direction of the first pinch element 61 and the second pinch element 62. Accordingly, gripping of the puncture section 70B by a user is not likely to be disturbed by the first pinch element 61 and the second pinch element 62.

Further, the puncture section 70 of the microneedle puncture instrument of the second modified example may not necessarily include the microneedle 72. Such a puncture section can serve as a press section as described below.

A microneedle puncture method by using the above pinch section 60 and a press section will now be described. In such a microneedle puncture method, two sites of the skin adjacent in the array direction Da are first pinched by the pinch section 60. Then, a microneedle is manually pressed against a position between the first pinch element 61 and the second pinch element 62 in the array direction Da by a user to thereby puncture the projections of the microneedle into the skin. After the user stops pressing the microneedle against the skin, the press section, located between the first pinch element 61 and the second pinch element 62 in the array direction Da, presses the microneedle against the skin from a position farther from the skin with the support shaft 63 of the pinch section 60 positioned therebetween while pinching the skin. Accordingly, the microneedle can be continuously pressed against the skin by the press section with a constant force.

A technical idea derived from the above modified examples is noted below.

[Note 1]

A microneedle puncture method including:

pinching a first portion and a second portion of the skin arrayed with an interval in an array direction by a pinch section in a pinch direction, which intersects with the array direction;

pressing a microneedle against a third portion located between the first portion and the second portion of the skin in the array direction; and pressing the microneedle against the third portion by a press section while pinching the third portion.

According to the above note, the microneedle can be continuously pressed against the skin by the press section with a constant force.

Third Modified Example

Figure 19:
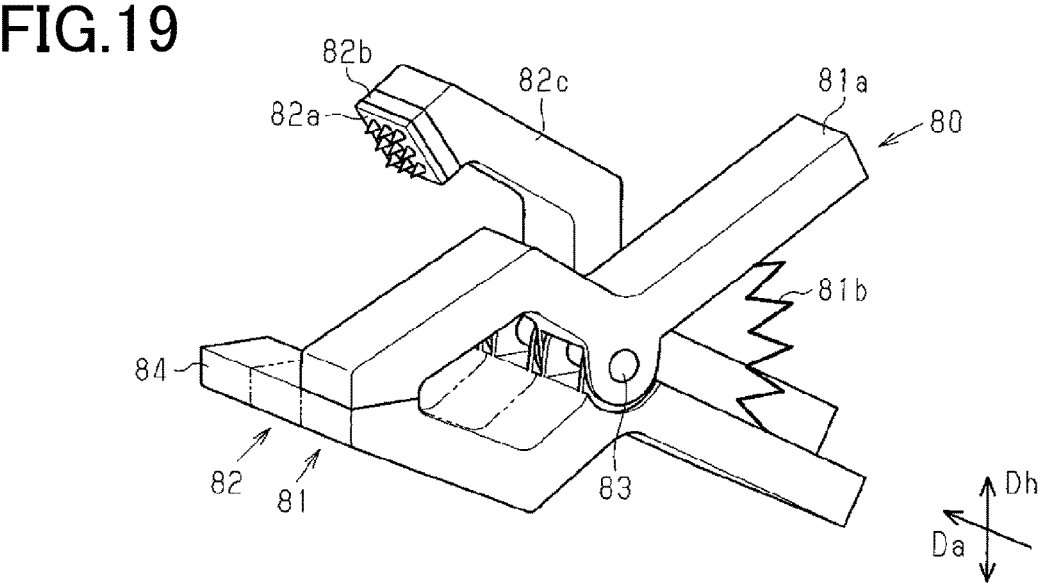
FIG. 19 is a perspective view illustrating a perspective structure of a third modified example.
Figure 20:
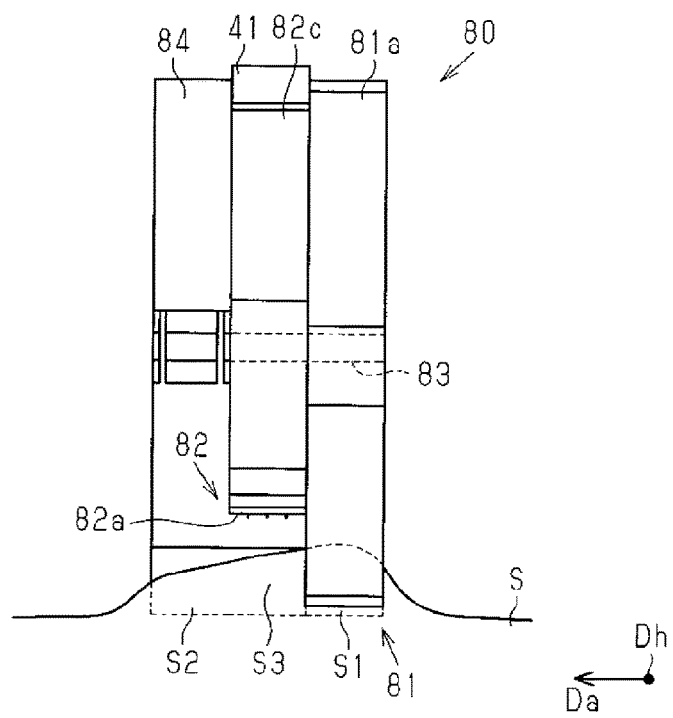
FIG. 20 is a diagram illustrating operation of the third modified example.

With reference to FIGS. 19 and 20, a third modified example of the microneedle puncture instrument will now be described.

The pinch section is not limited to a configuration having two pinch elements arrayed in the array direction Da, but may have an element corresponding to a single pinch element.

That is, as shown in FIG. 19, a microneedle puncture instrument 80 includes a pinch section 81 and a puncture section 82. The pinch section 81 includes an upper pinch portion and a lower pinch portion located at a position different from the upper pinch portion in the pinch direction Dh. The puncture section 82 includes a microneedle 82a for puncturing the skin, an upper puncture portion including a support portion 82b for supporting the microneedle 82a, and a lower puncture portion located at a position different from the upper puncture portion in the pinch direction Dh.

The pinch section 81 and the puncture section 82 are arrayed in the array direction Da, which intersects with the pinch direction Dh. The lower pinch portion and the lower puncture portion are included in a single lower portion, which extends in the array direction Da. The upper pinch portion and the upper puncture portion are located to face the same side of the lower portion. The lower portion has a portion extending in the array direction Da from a position facing the upper puncture portion to a side opposite to that facing the upper pinch portion.

More specifically, the upper pinch member 81a of the pinch section 81 and the upper puncture member 82c of the puncture section 82 are arrayed in the array direction Da. The upper pinch member 81a is an example of the upper pinch portion, and the upper puncture member 82c together with the support portion 82b is an example of the upper puncture portion. An end of the upper puncture member 82c in a direction intersecting with the array direction Da is provided with the support portion 82b such that the support portion 82b supports the microneedle 82a.

The microneedle puncture instrument 80 includes a support shaft 83 extending in the array direction Da, and a lower member 84 extending in the array direction Da and located at a position different from both the upper pinch member 81a and the upper puncture member 82c in the pinch direction Dh. The lower member 84 is an example of the lower portion.

In the pinch direction Dh, the upper pinch member 81a and the upper puncture member 82c are located to face the lower member 84 with the support shaft 83 positioned therebetween. The upper pinch member 81a, the upper puncture member 82c, and the lower member 84 are each supported by the support shaft 83.

The lower member 84 faces the upper pinch member 81a and the upper puncture member 82c in the pinch direction Dh. The lower member 84 has a size overlapping with both the upper pinch member 81a and the upper puncture member 82c in the array direction Da, and has a portion extending in the direction from a position facing the upper puncture member 82c to a side opposite to that faces the upper pinch member 81a. In other words, the lower member 84 has a portion extending in the array direction Da farther from the upper puncture member 82c so as to protrude from the upper puncture member 82c.

The portion of the lower member 84 protruding from the upper puncture member 82c in the array direction Da preferably has a length longer than that of the upper pinch member 81a in the array direction Da, but may be shorter than the length of the upper pinch member 81a.

The pinch section 81 and the puncture section 82 share the lower member 84. The portion of the lower member 84 facing the upper pinch member 81a in the pinch direction Dh serves as the pinch section 81, while the portion facing the upper puncture member 82c serves as the puncture section 82.

The pinch section 81 further includes a pinch bias member 81b such that one end of the pinch bias member 81b is connected to the upper pinch member 81a and the other end is connected to the lower member 84. Further, although not shown in the figure, the puncture section 82 also has a puncture bias member connected to the upper puncture member 82c and the lower member 84.

As shown in FIG. 20, in use of the microneedle puncture instrument 80 to puncture the skin by the microneedle 82a, the first portion S1 of the skin S is first pinched by the pinch section 81 while the upper puncture member 82c of the puncture section 82 is separated from the lower member 84 in the pinch direction Dh. Accordingly, not only the first portion S1 of the skin S, but also the second portion S2 which is spaced from the first portion S1 in the array direction Da, and the third portion S3 which is located between the first portion S1 and the second portion S2 and faces the upper puncture member 82c in the pinch direction Dh are also in contact with the lower member 84.

Thus, when the pinch section 81 pinches the first portion S1 of the skin S to fix the first portion S1, the first portion S1, the second portion S2, and the third portion S3 arrayed in the array direction Da are all supported by the lower member 84. The second portion S2 and the third portion S3 of the skin S which are in contact only with the lower member 84 are also fixed. In the second portion S2 and the third portion S3, the nearer the first portion S1, the more firmly fixed.

Then, the upper puncture member 82c is brought closer to the lower member 84 by a biasing force of the puncture bias member to thereby cause the microneedle 82a to puncture the third portion S3 of the skin S.

According to this configuration, the following effects can be obtained.

(6) When the microneedle 82a is punctured into the skin S, the pinch section 81 pinches the skin S and thus the sites on both sides of a portion of the skin S to be punctured by the microneedle 82a in the array direction Da is supported by the lower portion 84. Accordingly, when the microneedle 82a is punctured into the skin S, deformation of the skin S can be reduced since the skin S is supported by the lower portion 84. Further, while the pinch section 81 and the puncture section 82 pinch the skin S, a site which is in contact only with the lower portion 84, in addition to a site which is in contact with the upper pinch portion 81a and a site which is in contact with the upper puncture portion 82c, is fixed to a certain extent by the pinch section 81 and the puncture section 82. Accordingly, the microneedle 82a can be more easily held punctured into the skin S.

Fifth Modified Example

Each of the upper pinch member, the upper puncture member, and the lower pinch member are not limited to a shape extending in a single direction as described above, but may include a portion having a shape extending in a single direction and a portion having a plate shape.

Figure 21:
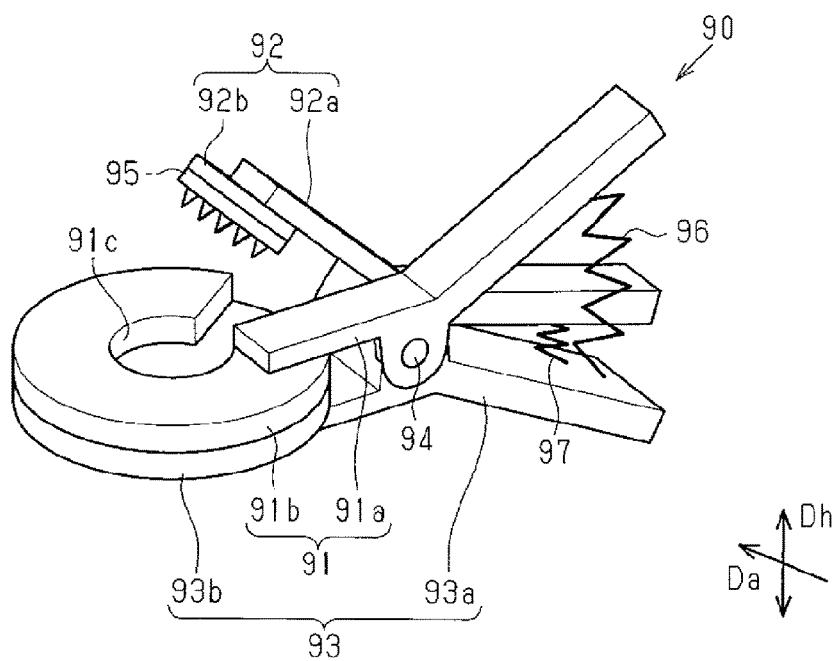
FIG. 21 is a perspective view illustrating a perspective structure of a fourth modified example.

That is, as shown in FIG. 21, a microneedle puncture instrument 90 includes the upper pinch member 91, the upper puncture member 92, and the lower member 93. The upper pinch member 91 includes a first portion 91a, and a second portion 91b connected to one end of the first portion 91a. The first portion 91a has a shape extending in a direction intersecting with the array direction Da, and is supported by a support shaft 94 extending in the array direction Da at a position in the middle of the longitudinal length of the first portion 91a extending in a direction intersecting with the array direction Da. The second portion 91b has an open annular shape as viewed in the pinch direction Dh. The region defined by the second portion 91b is an opening 91c, and the opening 91c has a circular shape as viewed in the pinch direction Dh.

The upper puncture member 92 includes a first portion 92a, and a second portion 92b connected to the first portion 92a. The first portion 92a has a shape extending in a direction parallel with the longitudinal direction of the upper pinch member 91. The first portion 92a is supported by the support shaft 94 at a position in the middle of the length extending in a direction parallel with the longitudinal direction of the upper pinch member 91. The second portion 92b is connected to an end of the first portion 92a on the same side as that of the upper pinch member 91 on which the second portion 91b is located as viewed from the support shaft 94. The second portion 92b has a disc shape when viewed in the pinch direction Dh, and the diameter of the second portion 92b is substantially the same as the diameter of the opening 91c defined by the second portion 91b of the upper pinch member 91. Further, the diameter of the second portion 92b may be any size, but not larger than the diameter of the opening 91c. The second portion 92b can support the microneedle 95 on the surface facing the lower member 93 in the second portion 92b. In other words, the second portion 92b serves as a support portion for supporting the microneedle 95.

The lower member 93 includes a first portion 93a, and a second portion 93b connected to the first portion 93a. As with the first portion 92a of the upper puncture member 92, the first portion 93a has a shape extending in a direction parallel with the longitudinal direction of the first portion 91a of the upper pinch member 91. The first portion 93a is supported by the support shaft 94 at a position in the middle of the length extending in a direction parallel with the longitudinal direction of the upper pinch member 91. The second portion 93b is connected to an end of the first portion 93a on the same side as that of the upper pinch member 91 on which the second portion 91b is located as viewed from the support shaft 94. The second portion 93b has a disc shape when viewed in the pinch direction Dh, and the diameter of the second portion 93b is equal to the diameter of the second portion 91b of the upper pinch member 91. Further, the diameter of the second portion 92b may be larger or smaller than the diameter of the second portion 91b of the upper pinch member 91.

A first bias member 96 and a second bias member 97 are disposed on the respective members on a side opposite to that having the second portion with the support shaft 94 interposed therebetween. The first bias member 96 is connected to the first portion 91a of the upper pinch member 91 and the first portion 93a of the lower member 93, and biases the upper pinch member 91 into a direction that causes the second portion 91b of the upper pinch member 91 and the second portion 93b of the lower member 93 to be in contact with each other. The second bias member 97 is connected to the first portion 92a of the upper puncture member 92 and the first portion 93a of the lower member 93, and biases the upper puncture member 92 into a direction that causes the second portion 92b of the upper puncture member 92 and the second portion 93b of the lower member 93 to be in contact with each other.

Accordingly, when a force in the direction that compresses the first bias member 96 is not applied to the first bias member 96, the second portion 91b of the upper pinch member 91 and the second portion 93b of the lower member 93 are in contact with each other. Further, when a force in the direction that compresses the second bias member 97 is not applied to the second bias member 97, the second portion 92b of the upper puncture member 92 and the second portion 93b of the lower member 93 pinch the microneedle 95.

In use of the microneedle puncture instrument 90 to puncture the skin, the distance between the first portion 91a of the upper pinch member 91 and the first portion 93a of the lower member 93 is first decreased to thereby allow the second portion 91b of the upper pinch member 91 and the second portion 93b of the lower member 93 to be separated from each other. Until the skin is punctured by the microneedle 95, the second portion 92b of the upper puncture member 92 is held spaced from the second portion 93b of the lower member 93. Then, while part of the skin is positioned between the second portion 91b of the upper pinch member 91 and the second portion 93b of the lower member 93, the distance between the first portion 91a of the upper pinch member 91 and the first portion 93a of the lower member 93 is increased to thereby allow the skin to be pinched by the upper pinch member 91 and the lower member 93. The distance between the first portion 92a of the upper puncture member 92 and the first portion 93a of the lower member 93 is then increased to thereby allow the microneedle 95 to be punctured into the skin. Here, the second portion 92b of the upper puncture member 92 is positioned within the opening 91c defined by the upper pinch member 91.

When the skin is punctured by the microneedle 95, the substantially entire area on the outer circumferential region of the puncture target is fixed by the lower member 93 and the upper pinch member 91. This facilitates puncture by the microneedle 95.

The fifth modified example can be further modified.

That is, a region defined by the second portion 91b of the upper pinch member 91 may be larger than a region occupied by the second portion 92b of the upper puncture member 92 when viewed in the pinch direction Dh. In other words, a region occupied by the second portion 92b of the upper puncture member 92 may be smaller than a region defined by the second portion 91b of the upper pinch member 91 when viewed in the pinch direction Dh.

Figure 22:
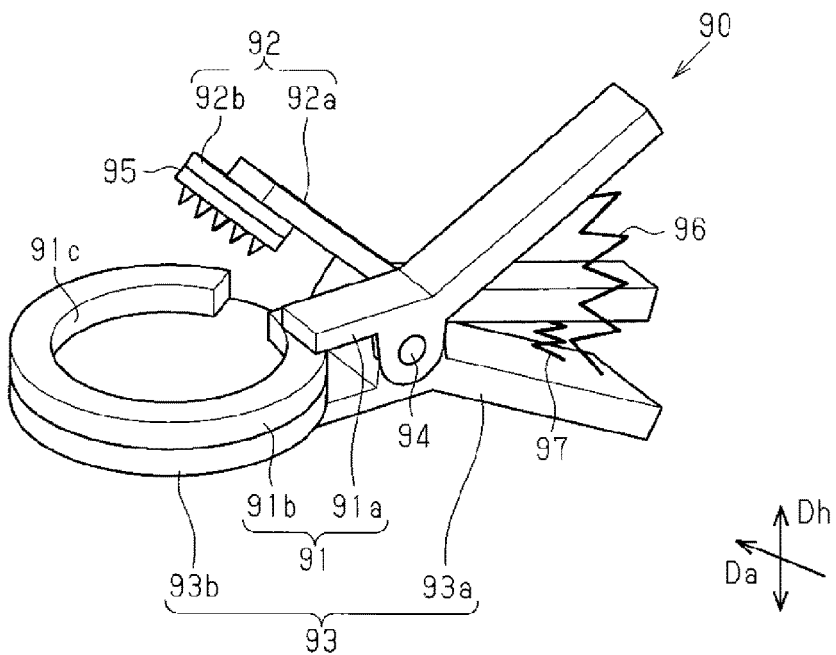
FIG. 22 is a perspective view illustrating a perspective structure of an example, which is a further modification of the fourth modified example.

For example, as shown in FIG. 22, the diameter of the second portion 91b of the upper pinch member 91 is equal to the diameter of the second portion 93b of the lower member 93, and the second portion 91b of the upper pinch member 91 defines the opening 91c having a diameter smaller than that of the upper second portion 91b. The diameter of the second portion 92b of the upper puncture member 92 is smaller than the diameter of the opening 91c. Accordingly, when the skin is punctured by the microneedle 95, a gap is formed on the entire circumference of the second portion 92b of the upper puncture member 92 between the second portion 92b of the upper puncture member 92 and the second portion 91b of the upper pinch member 91.

Sixth Modified Example

As described below referring to FIG. 23, the microneedle puncture instrument may be configured as a sixth modified example. The sixth modified example differs from the fifth modified example in the configuration of the lower pinch member.

Figure 23:
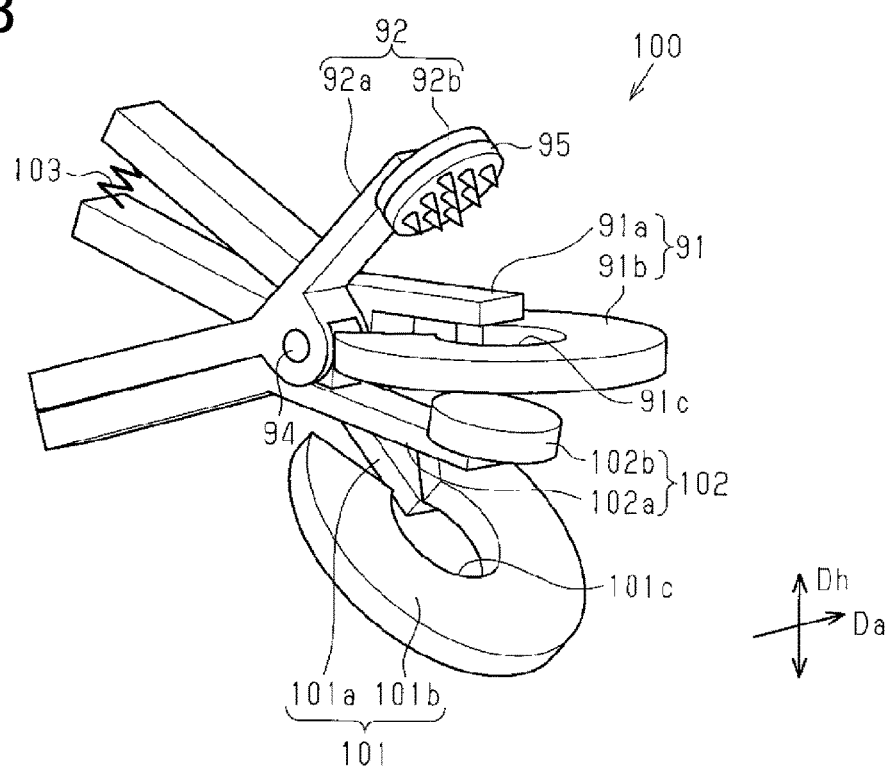
FIG. 23 is a perspective view illustrating a perspective structure of a fifth modified example.

As shown in FIG. 23, a microneedle puncture instrument 100 includes a first lower member 101 and a second lower member 102 in addition to the upper pinch member 91 and the upper puncture member 92. The upper pinch member 91 and the upper puncture member 92 each have the same configuration as that of the upper pinch member 91 and the upper puncture member 92 as described in the fifth modified example.

The first lower member 101 includes a first portion 101a and a second portion 101b connected to the first portion 101a. The first portion 101a has a shape extending in a direction parallel with the longitudinal direction of the first portion 91a of the upper pinch member 91. The first portion 101a is supported by the support shaft 94 at a position in the middle of the length extending in a direction parallel with the longitudinal direction of the upper pinch member 91. The second portion 101b is connected to an end of the first portion 101a on the same side as that of the upper pinch member 91 on which the second portion 91b is located as viewed from the support shaft 94. The second portion 101b has an open annular shape when viewed in the pinch direction Dh, and the diameter of the second portion 101b is equal to the diameter of the second portion 91b of the upper pinch member 91. Further, the diameter of the second portion 101b may be larger or smaller than the diameter of the second portion 91b of the upper pinch member 91. The region defined by the second portion 101b is an opening 101c, and the opening 101c has a circular shape as viewed in the pinch direction Dh. When the upper pinch member 91 and the first lower member 101 are in contact with each other, the opening 91c defined by the upper pinch member 91 overlaps with the opening 101c defined by the first lower member 101.

The second lower member 102 includes a first portion 102a and a second portion 102b connected to the first portion 102a. The first portion 102a has a shape extending in a direction parallel with the longitudinal direction of the first portion 101a of the first lower member 101. The first portion 102a is supported by the support shaft 94 at a position in the middle of the length extending in a direction parallel with the longitudinal direction of the first lower member 101. The second portion 102b is connected to an end of the first portion 102a on the same side as that of the first lower member 101 on which the second portion 101b is located as viewed from the support shaft 94. The second portion 102b has a disc shape when viewed in the pinch direction Dh, and the diameter of the second portion 102b is substantially the same as the diameter of the opening 101c defined by the second portion 101b of the first lower member 101. Further, the diameter of the second portion 102b may be any size, but not larger than the diameter of the opening 101c.

A first bias member 103 and a second bias member, not shown in the figure, are disposed on the respective members on a side opposite to that having the second portion with the support shaft 94 interposed therebetween. The first bias member 103 is connected to the first portion 91a of the upper pinch member 91 and the first portion 101a of the first lower member 101, and biases the upper pinch member 91 into a direction that causes the second portion 91b of the upper pinch member 91 and the second portion 101b of the first lower member 101 to be in contact with each other. The second bias member is connected to the first portion 92a of the upper puncture member 92 and the first portion 102a of the second lower member 102, and biases the upper puncture member 92 into a direction that causes the second portion 92b of the upper puncture member 92 and the second portion 102b of the second lower member 102 to be in contact with each other.

Accordingly, when a force in the direction that compresses the first bias member 103 is not applied to the first bias member 103, the second portion 91b of the upper pinch member 91 and the second portion 101b of the first lower member 101 are in contact with each other. Further, when a force in the direction that compresses the second bias member is not applied to the second bias member, the second portion 92b of the upper puncture member 92 and the second portion 102b of the second lower member 102 pinch the microneedle 95.

In use of the microneedle puncture instrument 100 to puncture the skin, the distance between the first portion 91a of the upper pinch member 91 and the first portion 101a of the lower member 101 is first decreased to thereby allow the second portion 91b of the upper pinch member 91 and the second portion 101b of the first lower member 101 to be separated from each other. Until the skin is punctured by the microneedle 95, the second portion 92b of the upper puncture member 92 is held spaced from the second portion 102b of the second lower member 102. Then, while part of the skin is positioned between the second portion 91b of the upper pinch member 91 and the second portion 101b of the first lower member 101, the distance between the first portion 91a of the upper pinch member 91 and the first portion 101a of the first lower member 101 is increased to thereby allow the skin to be pinched by the upper pinch member 91 and the first lower member 101. The distance between the first portion 92a of the upper puncture member 92 and the first portion 102a of the second lower member 102 is then increased to thereby allow the microneedle 95 to be punctured into the skin. Here, the second portion 92b of the upper puncture member 92 is located within the opening 91c defined by the upper pinch member 91, and the second portion 102b of the second lower member 102 is located within the opening 101c of the first lower member 101.

According to the microneedle puncture instrument 100, an effect similar to the microneedle puncture instrument 90 of the fifth modified example can be obtained.

Other Modified Examples

The foregoing embodiment can be appropriately modified and implemented as described below.

The pinch section 11 and the puncture section 12 are not necessarily supported by a single shaft as long as the puncture section 12 is connected to the pinch section 11 at a position between the first pinch element 11a and the second pinch element 11b in the array direction Da. That is, the support shaft of the pinch section 11 and the support shaft of the puncture section 12 may extend in parallel with each other, or the support shaft of the pinch section 11 and the support shaft of the puncture section 12 may extend in directions intersecting with each other. In this configuration as well, an effect similar to the above (4) can be achieved.

The first pinch element 11a may not necessarily include the first upper member 22a and the first lower member 22b as separate members. Alternatively, the first pinch element 11a may be configured as a single member that includes the first upper portion and the first lower portion.

As with the first pinch element 11a, the second pinch element 11b may not necessarily include the second upper member 23a and the second lower member 23b as separate members. Alternatively, the second pinch element 11b may be configured as a single member that includes the second upper portion and the second lower portion.

As with the first pinch element 11a, the puncture section 12 may not necessarily include the upper puncture member 31a and the lower puncture member 31b as separate members. Alternatively, the puncture section 12 may be configured as a single member that includes the upper puncture portion and the lower puncture portion.

When the first pinch element 11a, the second pinch element 11b, and the puncture section 12 are each configured as a single member that includes the upper portion and the lower portion, the single member may be fixed to the support shaft.

The first pinch element 11a, the second pinch element 11b, and the puncture section 12 may also be each configured as a single member that includes a bias portion corresponding to the bias member, in addition to the upper portion and the lower portion.

When the first pinch element 11a, the second pinch element 11b, and the puncture section 12 are each configured as a single member that include the upper portion, the lower portion, and the bias portion, the bias portion of the single member may be fixed to the support shaft.

When the first pinch element 11a and the second pinch element 11b are configured to have the distance Dist maintained at a constant distance, the relative position of the first pinch element 11a to the support shaft 21 and the relative position of the second pinch element 11b to the support shaft 21 may be variable.

When the first pinch element 11a and the second pinch element 11b are configured to have the distance Dist maintained within a predetermined range, the microneedle puncture instrument 10 may include a regulation section in the support shaft 21 to regulate the positions of the first upper member 22a and the first lower member 22b. In addition, the microneedle puncture instrument 10 may include a regulation section in the support shaft 21 to regulate the positions of the second upper member 23a and the second lower member 23b within a predetermined range. In this configuration as well, an effect which is the same as that of the above (1) can be achieved.

As long as the first pinch element 11a and the second pinch element 11b are arrayed in the array direction Da, the first pinch element 11a and the second pinch element 11b may not be supported by a single shaft. That is, the support shaft of the first pinch element 11a and the support shaft of the second pinch element 11b may be configured to extend in directions parallel with each other, or the support shaft of the first pinch element 11a and the support shaft of the second pinch element 11b may be configured to extend in directions intersecting with each other. In this configuration as well, an effect which is the same as that of the above (1) can be achieved.

The lower supported pieces of each of the first lower member 22b, the second lower member 23b, and the lower puncture member 31b may be supported by the support shaft 21 in a manner rotatable about the support shaft 21. Alternatively, while these lower supported pieces are supported by the support shaft 21 in a manner rotatable about the support shaft 21, the upper supported pieces of the first upper member 22a, second upper member 23a, and the upper puncture member 31a may be supported by the support shaft 21 in a manner so as not to rotate about the support shaft 21. In such configurations as well, the first pinch element 11a, second pinch element 11b, and the puncture section 12 can pinch the skin S.

The area of the support portion 12b and the area of the base 12a1 of the microneedle 12a may not be each necessarily equal to the upper puncture end 31a2. For example, these areas may be each larger than the area of the upper puncture end 31a2.

Figure 24:
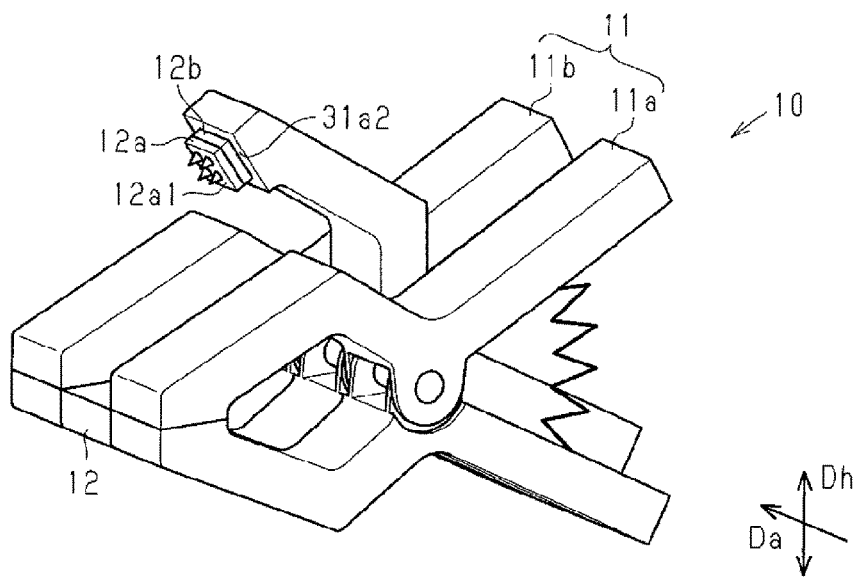
FIG. 24 is a perspective view illustrating a perspective structure according to another modified example.

Alternatively, as shown in FIG. 24, the area of the support portion 12b and the area of the base 12a1 of the microneedle 12a may be each smaller than the area of the upper puncture end 31a2. Further, the area of the support portion 12b and the area of the base 12a1 of the microneedle 12a may be different from each other.

REFERENCE SIGNS LIST 10, 50, 50A, 50B, 50C, 80, 90, 100 . . . Microneedle puncture instrument; 11, 60, 81 . . . Pinch section; 11a, 51, 61 . . . First pinch element; 11b, 52, 62 . . . Second pinch element; 12, 53, 70, 70A, 70B, 8 . . . Puncture section; 12a, 53b, 72, 82a, 95 . . . Microneedle; 12a1 . . . Base; 12a2 . . . Projection; 12b, 53c, 71d, 82b . . . Support portion; 21, 55, 63, 73, 83, 94 . . . Support shaft; 21a . . . First shaft portion; 21b . . . Second shaft portion; 21c . . . Third shaft portion; 22 . . . First pinch section; 22a, 51a, 51c1, 61a . . . First upper member; 22a1, 23a1, 31a1, A13, B13 . . . Upper supported piece; 22a2, 23a2, a131 . . . Upper pinch end; 22b, 61b, 101 . . . First lower member; 22b1, 23b1, 31b1, A23, B23 . . . Lower supported piece; 22b2, 23b2, 54b1 . . . Lower pinch end; 23 . . . Second pinch section; 23a, 51c2, 52a, 62a . . . Second upper member; 23b, 62b, 102 . . . Second lower member; 24, 51b, 61c, 96, 103 . . . First bias member; 25, 62c, 97 . . . Second bias member; 31a, 53a, 53a1, 70A1, 70B1, 71a, 82c . . . Upper puncture member; 31a2, 53a2 . . . Upper puncture end; 31b, 70A2, 70B2, 71b . . . Lower puncture member; 31b2 . . . Lower puncture end; 32, 71c . . . Puncture bias member; 41 . . . Stopper; 54, 54b, 84, 93 . . . Lower member; Mal, 81a, 91, 92 . . . Upper pinch member; 81b . . . Pinch bias member; 91a, 92a, 93a, 101a, 102a, a11, A11, A21, B11, B21 . . . First portion; 91b, 92b, 93b, 101b, 102b, a12, A12, A22, B12, B22 . . . Second portion; 91c, 101c . . . Opening; a13 . . . Third portion; a13a . . . First distal portion; a13b . . . Second distal portion.

What is claimed is:

1. A microneedle puncture instrument comprising:
   a pinch section including a first pinch element and a second pinch element arrayed in an array direction and configured to individually pinch a skin in a pinch direction, which intersects with the array direction, the first pinch element and the second pinch element being connected to each other with a distance therebetween maintained within a predetermined range; and
   a puncture section configured to puncture the skin while pinching the skin in the pinch direction at a position between the first pinch element and the second pinch element in the array direction, the puncture section including a microneedle for puncturing the skin and a support portion that supports the microneedle.

2. The microneedle puncture instrument of claim 1, further comprising a support shaft that extends in the array direction, and
   wherein the pinch section includes:
   a first pinch section supported by a first shaft portion which is part of the support shaft, the first pinch section including a first upper portion, and a first lower portion located at a position different from the first upper portion in the pinch direction, the first upper portion and the first lower portion cooperating with each other to pinch the skin; and a second pinch section supported by a second shaft portion which is part of the support shaft, the second pinch section including a second upper portion, and a second lower portion located at a position different from the second upper portion in the pinch direction, the second upper portion and the second lower portion cooperating with each other to pinch the skin, the first pinch element includes the first shaft portion and the first pinch section, and the second pinch element includes the second shaft portion and the second pinch section.

3. The microneedle puncture instrument of claim 2, wherein the puncture section includes:

a third shaft portion which is part of the support shaft located between the first shaft portion and the second shaft portion in the array direction;

an upper puncture portion supported by the third shaft portion and including the support portion; and a lower puncture portion located at a position different from the upper puncture portion in the pinch direction, and the upper puncture portion and the lower puncture portion cooperate with each other to pinch the skin.

4. The microneedle puncture instrument of claim 1, wherein the puncture section is connected to the pinch section at a position between the first pinch element and the second pinch element in the array direction.

5. The microneedle puncture instrument of claim 4, further comprising:

three upper portions arrayed in the array direction; and a lower portion extending in the array direction and located at a position different from all three upper portions in the pinch direction, the lower portion having a size overlapping with all three upper portions in the array direction when viewed in the pinch direction, wherein the first pinch element, the second pinch element, and the puncture section each have individual upper portions of the three upper portions, wherein the upper portion of the puncture section includes the support portion, and wherein the pinch section and the puncture section share the lower portion.

6. A microneedle puncture instrument, comprising:

a pinch section configured to pinch a skin in a pinch direction, the pinch section including an upper pinch portion and a lower pinch portion located at a position different from the upper pinch portion in the pinch direction; and a puncture section configured to puncture the skin while pinching the skin in the pinch direction, the puncture section including an upper puncture portion which includes a microneedle for puncturing the skin and a support portion that supports the microneedle, and a lower puncture portion located at a position different from the upper puncture portion in the pinch direction, wherein the pinch section and the puncture section are arrayed in an array direction, which intersects with the pinch direction, wherein the lower pinch portion and the lower puncture portion are included in a single lower portion extending in the array direction, wherein the upper pinch portion and the upper puncture portion are located to face a same side of the single lower portion, and wherein the single lower portion has a portion extending in the array direction from a position facing the upper puncture portion to a side opposite to that facing the upper pinch portion.

* * * * *